(12) United States Patent
Keswani et al.

(10) Patent No.: US 11,013,787 B2
(45) Date of Patent: May 25, 2021

(54) SUSTAINED RELEASE FORMULATION OF INTERLEUKIN-10 FOR WOUND TREATMENT AND RELATED METHODS

(71) Applicant: CHILDREN'S HOSPITAL MEDICAL CENTER, Cincinnati, OH (US)

(72) Inventors: Sundeep Govind Keswani, Cincinnati, OH (US); Paul Laszlo Bollyky, Stanford, CA (US); Swathi Balaji, Cincinnati, OH (US); Timothy M. Crombleholme, Denver, CO (US)

(73) Assignees: CHILDREN'S HOSPITAL MEDICAL CENTER, Cincinnati, OH (US); THE BOARD OF TRUSTEES OF THE LELAND STANFORD JUNIOR UNIVERSITY, Stanford, CA (US); THE REGENTS OF THE UNIVERSITY OF COLORADO FOR AND ON BEHALF OF THE UNIVERSITY OF COLORADO DENVER, Denver, CO (US)

( * ) Notice: Subject to any disclaimer, the term of this patent is extended or adjusted under 35 U.S.C. 154(b) by 0 days.

(21) Appl. No.: 16/160,742

(22) Filed: Oct. 15, 2018

(65) Prior Publication Data
US 2019/0046612 A1 Feb. 14, 2019

Related U.S. Application Data

(62) Division of application No. 14/449,657, filed on Aug. 1, 2014, now Pat. No. 10,098,929.

(60) Provisional application No. 61/861,847, filed on Aug. 2, 2013.

(51) Int. Cl.
| | | |
|---|---|---|
| A61K 38/20 | (2006.01) | |
| A61K 47/36 | (2006.01) | |
| A61K 47/42 | (2017.01) | |
| A61K 47/10 | (2017.01) | |
| A61K 9/00 | (2006.01) | |
| A61K 9/06 | (2006.01) | |

(52) U.S. Cl.
CPC ........ *A61K 38/2066* (2013.01); *A61K 9/0014* (2013.01); *A61K 9/06* (2013.01); *A61K 47/10* (2013.01); *A61K 47/36* (2013.01); *A61K 47/42* (2013.01)

(58) Field of Classification Search
CPC ................................................. A61K 38/2066
See application file for complete search history.

(56) References Cited

U.S. PATENT DOCUMENTS 7,052,684 B2  5/2006  Ferguson
2008/0139478 A1  6/2008  Ferguson et al.

OTHER PUBLICATIONS

Baldrick, Paul. "Pharmaceutical excipient development: The need for preclinical guidance." *Regulatory toxicology and pharmacology* 32.2 (2000): 210-218.
Beausang, E., et al. "A new quantitative scale for clinical scar assessment." *Plastic and reconstructive surgery* 102.6 (1998): 1954-1961.
Berg, Daniel J., et al. "Interleukin 10 but not interleukin 4 is a natural suppressant of cutaneous inflammatory responses." *Journal of Experimental Medicine* 182.1 (1995): 99-108.
Bogdan, Christian, Yoram Vodovotz, and Cad Nathan. "Macrophage deactivation by interleukin 10." *Journal of Experimental Medicine* 174.6 (1991): 1549-1555.
Charman, William N. "Lipids, lipophilic drugs, and oral drug delivery—some emerging concepts." *Journal of pharmaceutical sciences* 89.8 (2000): 967-978.
Chernoff, Amy E., et al. "A randomized, controlled trial of IL-10 in humans. Inhibition of inflammatory cytokine production and immune responses." *The Journal of Immunology* 154.10 (1995): 5492-5499.
Fiorentino, David F., Martha W. Bond, and T. R. Mosmann. "Two types of mouse T helper cell. IV. Th2 clones secrete a factor that inhibits cytokine production by Th1 clones." *Journal of Experimental Medicine* 170.6 (1989): 2081-2095.
Go, Ning Fei, et al. "Interleukin 10, a novel B cell stimulatory factor: unresponsiveness of X chromosome-linked immunodeficiency B cells." *Journal of Experimental Medicine* 172.6 (1990): 1625-1631.
Kim, Jenny M., et al. "Structure of the mouse IL-10 gene and chromosomal localization of the mouse and human genes." *The Journal of Immunology* 148.11 (1992): 3618-3623.
Moore, Kevin W., et al. "Homology of cytokine synthesis inhibitory factor (IL-10) to the Epstein-Barr virus gene BCRFI." *Science* 248.4960 (1990): 1230.
O'Garra, Anne, et al. "Production of cytokines by mouse B cells: B lymphomas and normal B cells produce interleukin 10." *International Immunology* 2.9 (1990): 821-832.
Remington, Joseph Price. *Remington: The science and practice of pharmacy.* vol. 1. Lippincott Williams & Wilkins, 2006.
Rowe, Raymond C., Paul J. Sheskey, and Paul Weller, eds. *Handbook of pharmaceutical excipients.* vol. 6. London: Pharmaceutical press, 2006.
Van Vlasselaer, P., et al. "Interleukin 10 inhibits transforming growth factor-beta (TGF-beta) synthesis required for osteogenic commitment of mouse bone marrow cells." *The Journal of cell biology* 124.4 (1994): 569-577.
Van Zuijlen. P. P., et al "Scar assessment tools: implications for current research." *Plastic and reconstructive surgery* 109.3 (2002): 1108-1122.
Vieira, P., et al. "Isolation and expression of human cytokine synthesis inhibitory factor cDNA clones: homology to Epstein-Barr virus open reading frame BCRFI." *Proceedings of the National Academy of Sciences* 88.4 (1991): 1172-1176.

(Continued)

*Primary Examiner* — Prema M Mertz
(74) *Attorney, Agent, or Firm* — Knobbe, Martens, Olson & Bear, LLP

(57) ABSTRACT

A sustained release formulation of interleukin-10 for wound treatment and related methods is provided.

18 Claims, 9 Drawing Sheets

(56) References Cited

OTHER PUBLICATIONS

Balaji, et al. The role of interleukin-10 and hyaluronan in murine fetal fibroblast function in vitro: implications for recapitulating fetal regenerative wound healing, PLoS One 10(5), 2015, pp. 1-17.
Prosdocimi, et al. "Exogenous hyaluronic acid and wound healing: an updated version", (2012), Paniminerva Med, 2012, 54:129-135.
Kieran, et al. "Interleukin-10 reduces scar formation in both animal and human cutaneous wounds: results of two preclinical and phase II randomized control studies" Wound Rep Reg, 2013, 21 (3):428-436.
Price, et al. "The role of hyaluronic acid in wound healing" Am J Clin Dermatol, 2005, 6(6): 393-402.

SUSTAINED RELEASE FORMULATION OF INTERLEUKIN-10 FOR WOUND TREATMENT AND RELATED METHODS

STATEMENT REGARDING FEDERALLY SPONSORED R&D

This invention was made with government support under GM098831 awarded by the National Institutes of Health. The government has certain rights in the invention.

INCORPORATION BY REFERENCE TO ANY PRIORITY APPLICATIONS

Any and all priority claims identified in the Application Data Sheet, or any correction thereto, are hereby incorporated by reference under 37 CFR 1.57.

BACKGROUND

Field

This disclosure is directed to a sustained release formulation of interleukin-10 (IL-10) for wound treatment and related methods.

Description of the Related Technology

Each year, 100 million patients acquire scars, some of which cause considerable morbidity, including loss of physical function, reduced tissue integrity and in some disease states a predisposition to repetitive injury.

Scarring is the normal process by which postnatal mammals heal wounds. It is initiated by an inflammatory response followed by fibroblast mediated deposition of collagen with subsequent remodeling. Scars are characterized by haphazard collagen deposition, a flattened epidermis and a dropout of dermal appendages. These scars can have significant functional and psychosocial sequelae. Currently, there is a significant unmet market need for an effective skin regenerating, anti-scarring agent.

Prenatal mammals heal dermal wounds without scar and is characterized by an attenuated inflammatory response. Reverting the wound environment of the postnatal scarring phenotype to a more "fetal-type" milieu to achieve scarless tissue repair is of interest.

In view of the limitation of present treatments, there exists a desire for development of new methods and products useful for treating wounds.

SUMMARY

Some embodiments provide methods for treating wounds with sustained release formulations of interleukin-10.

Some embodiments provide methods for preventing or reducing scarring or fibrosis with sustained release formulations of interleukin-10.

Some embodiments provide an extended release biocompatible composition for preventing or reducing scarring of an incision or wound site in a subject, comprising: a biodegradable support scaffold; and IL-10, wherein the amount of IL-10 in the composition is from about 0.2 µM to about 2.5 µM.

Some embodiments provide an extended release biocompatible composition for preventing or reducing scarring of an incision or wound site in a subject, comprising: a biodegradable support scaffold; and IL-10, wherein the biodegradable support scaffold is configured to release from about 0.015 nM to about 0.015 µM of IL-10 over a period of time at the incision or wound site.

Some embodiments provide a method for preventing or reducing scarring or process characterized by fibroplasia including but not limited to post surgical wounds, traumatic wounds, keloids, hypertrophic scars, burn contractures, solid organ fibrosis, and intraabdominal adhesions by administering a therapeutically effective amount of IL-10 to a location in a subject for a period of time sufficient to prevent or reduce scarring or fibrosis, said administering comprising a single administration of a composition as disclosed and described herein to an incision or wound site in the subject. Some such embodiments provide a method for preventing or reducing scarring or process characterized by excessive fibroplasia including but not limited to pathologic scars and keloids.

Some embodiments provide a method for preventing or reducing scarring or process characterized by fibroplasia by administering a therapeutically effective amount of IL-10 to a location in a subject for a period of time sufficient to prevent or reduce scarring or fibrosis, said administering comprising administration of the as disclosed and described herein to a site at risk for fibroplasia in the subject. Some such embodiments provide a method for preventing or reducing scarring or process characterized by excessive fibroplasia including but not limited to pathologic scars and keloids.

Some embodiments provide a method for preventing or reducing scarring of an incision or wound comprising administering a therapeutically effective amount of IL-10 to a location in a subject for a period of time sufficient to prevent or reduce scarring, said administering comprising a single administration of the composition of any one of the preceding claims to an incision or wound site in the subject.

Some embodiments provide method for preventing or reducing scarring of an incision or wound in a subject, comprising: providing the composition as disclosed and described herein; and introducing the composition to a location by administration of the composition; and maintaining an amount of IL-10 for a period of time sufficient to prevent or reduce scarring at the location.

Some embodiments provide a method for preventing or reducing scarring of an incision or wound in a subject, comprising: providing a composition as disclosed and described herein; and introducing the composition to a location in a single administration; and maintaining an amount of IL-10 for a period of time sufficient to prevent or reduce scarring at the location.

Some embodiments provide a method for preventing or reducing scarring of an incision or wound comprising administering a therapeutically effective amount of IL-10 to a location in a subject for a period of time sufficient to prevent or reduce scarring, said administering comprising administration of the composition as disclosed and described herein to an incision or wound site in the subject.

In some embodiments, the type of wound to be treated with the extended release biocompatible composition can be a penetrating type wound, such as, for example, a puncture, laceration, or bullet or shrapnel wound. In some embodiments, the type of wound to be treated with the extended release biocompatible composition can be a non-penetrating type wound, such as, for example, grazes, abrasions, skin grafts, or burns.

In some embodiments, the type of wound to be treated with the extended release biocompatible composition can be a laceration or other open type wound. For example, an individual or medical aid personnel can treat the wound by utilizing a system comprising a topically-applied source of an extended release biocompatible composition and a surgical dressing.

Some embodiments provide a kit comprising: an extended release biocompatible composition and a dressing. In some aspects, the dressing can be a surgical dressing. In some aspects, the dressing can be a field dressing.

Some embodiments provide a method of evaluating a composition for treating a wound including: providing a dosage of the composition to a wound in a statistically relevant number of animals; and evaluating the wound in each animal after a period of time using an Assessment Scale value to obtain an Assessment Scale score, wherein said Assessment Scale score is based on the measurement of at least 2 parameters selected from the group consisting of i) the quantification of topography, ii) epidermal height, and iii) the nuclear orientation of the basal keratinocytes in the epidermis; and iv) the quantification of the scar area, v) dermal appendages, and vi) vascularity (vessel density) in the dermis of the scars. In some embodiments, each parameter is calculated to provide an Assessment Scale value (INDEX), wherein an Assessment Scale score is calculated by ("Σ INDEX/n)×100 where n is the number of parameters being evaluated.

It is provided that, in some embodiments, when IL-10 is discussed in the specification and claims that the IL-10 related peptides disclosed in US. Publication No. 2008/0139478 or a fragment or partially modified form of IL-10 disclosed in U.S. Pat. No. 7,052,684, the relevant disclosures of which are incorporated herein in their entireties, may be included in place of IL-10 in the compositions or methods as disclosed and described herein.

DETAILED DESCRIPTION

Figure 1A:
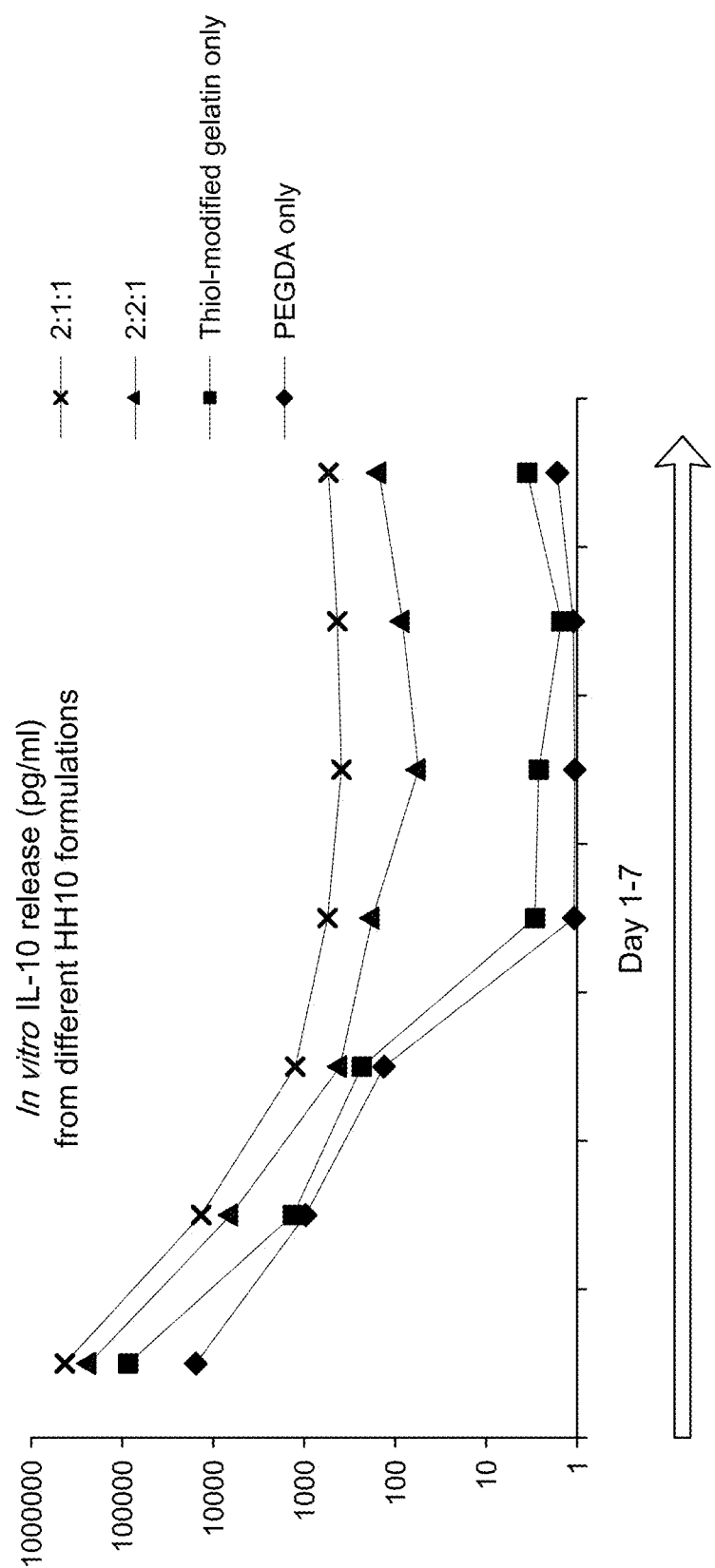
FIGS. 1(A) and (B) depict in vitro and in vivo properties of sustained release of rIL-10.

This disclosure relates to treating wounds and preventing or reducing fibrosis with an extended release biocompatible composition suitable for directly introducing into a wound and/or as a topical application.

As used herein the term "wounds" refers to any condition which may result in fibrosis. In particular, this includes fibrosis resulting from an injury or surgery.

As used herein the term "fibrosis" refers to the formation of excess fibrous connective tissue in an organ or tissue in a reparative or reactive process. This can be a reactive, benign, or pathological state. In response to injury this is called scarring and if fibrosis arises from a single cell line this is called a fibroma. Physiologically this acts to deposit connective tissue, which can obliterate the architecture and function of the underlying organ or tissue. Fibrosis can be used to describe the pathological state of excess deposition of fibrous tissue, as well as the process of connective tissue deposition in healing. Examples of fibrosis include, but are not limited to, pulmonary fibrosis, glomerulonephritis, cirrhosis of the liver, systemic sclerosis, scleroderma, proliferative vitreoretinopathy, and scar tissue formed as a result of injury, surgery, or burn.

While not bound by any theory, it is believed that the beneficial effects of the recited compositions may be achieved through biological activity of Interleukin-10 (IL-10) inhibiting inflammation at a wound site.

IL-10 was identified as a product of Th2 cells (Fiorentino, D. F. and Moddman, T. R., 1989, J. Exp. Med., 170: 2081 2095) and identified as a product of B-cell lymphomas that prolonged the survival of mast cells and enhanced proliferation of thymocytes (O'Garra, A. et al., 1990, Internal Immunol., 2: 821 823).

Molecular characterization of human and murine IL-10 by Moore, K. W. et al. (1990, Science, 248: 1230 1234) and Vieira, P. et al. (1991, Proc. Natl. Acad. Sci. USA, 88: 1172 1176) showed that there was an 80% homology of their nucleotide sequences. Mouse IL-10 (mIL-10) protein consists of 157 amino acids with two potential N-glycosylation sites although glycosylation is not essential for the biological activities of mIL-10. Human IL-10 (hIL-10) protein consists of 160 amino acids with one potential N-glycosylation site which is not used (Vieira et al., 1991). Both mIL-10 and hIL-10 contain four cysteine residues that form two intramolecular disulphide bonds generating biologically active homodimers with molecular weights of 32 kDa and 39 kDa respectively. Although there is 80% homology between hIL-10 and mIL-10, only hIL-10 acts on both human and mouse cells, whereas mIL-10 has species specificity activity (Vieira et al., 1991; Kim, J. M. et al., 1992, J. Inmunol., 148: 3618 3623).

There are many cellular sources and major biological activities of IL-10, all of which may play some role in the wound microenvironment. It has been shown that IL-10 possesses many stimulatory and inhibitory effects. For example, van Vlasselar et al. (1994, J. Cell Biol., 124: 569 577) showed that IL-10 inhibited TGF-β synthesis required for osteogenic commitment of mouse bone marrow cells, and hence the resulting mineralized matrix, whereas Go et al (1990, J. Exp. Med., 172: 1625 1631) showed IL-10 to be a novel B-cell stimulatory factor. IL-10 has also been shown by Bogdan et al. (1991, J. Exp. Med., 174: 1549 1555) to directly act on macrophages and inhibit their subsequent activation and hence release of pro-inflammatory cytokines (see also Berg. D. J. et al., 1995, J. Exp. Med., 182: 99 10; Chemoff, A. E. et al., 1995, J. Immunol. 154 (10): 5492 5499).

Some embodiments relate to a method for treating a wound. In some embodiments, the wound is a postsurgical wound. In some embodiments, the wound is a trauma wound. In some embodiments, the method of treating the wound can comprise: introducing an extended release biocompatible composition into the wound.

Some embodiments provide an extended release biocompatible composition for preventing or reducing scarring of an incision or wound site in a subject, comprising: a biodegradable support scaffold; and IL-10, wherein the amount of IL-10 in the composition is from about 0.2 μM to about 2.5 μM.

Some embodiments provide an extended release biocompatible composition for preventing or reducing scarring of an incision or wound site in a subject, comprising: a biodegradable support scaffold; and IL-10, wherein the amount of IL-10 in the composition is from about 0.2 μM to about 2.5 μM.

In some embodiments, the extended release biocompatible composition comprises an amount of biodegradable support scaffold from about 10% to about 59% based on the total amount of the extended release biocompatible composition. In some embodiments, the extended release biocompatible composition comprises an amount of biodegradable support scaffold from about 15% to about 85% based on the total amount of the extended release biocompatible composition. In some embodiments, the extended release biocompatible composition comprises an amount of biodegradable support scaffold from about 20% to about 80% based on the total amount of the extended release biocompatible composition. In some embodiments, the extended release biocompatible composition comprises an amount of biodegradable support scaffold based on the total amount of the extended release biocompatible composition of about 10%, 15%, 20%, 25%, 30%, 35%, 40%, 45%, 50%, 55%, 60%, 65%, 70%, 75%, 80%, 85% or 90% or a range defined by any two of the preceding values.

In some embodiments, the biodegradable support scaffold comprises hyaluronan or a hyaluronan moiety. In some embodiments, the hyaluronan is hyaluronic acid. In some embodiments, the biodegradable support scaffold comprises an amount of hyaluronan or a hyaluronan moiety from about 10% to about 90% based on the total amount of the biodegradable support scaffold. In some embodiments, the biodegradable support scaffold comprises an amount of hyaluronan or a hyaluronan moiety from about 10% to about 90% based on the total amount of the biodegradable support scaffold. In some embodiments, the biodegradable support scaffold comprises an amount of hyaluronan or a hyaluronan moiety from about 30% to about 70% based on the total amount of the biodegradable support scaffold. In some embodiments, the biodegradable support scaffold comprises an amount of hyaluronan or a hyaluronan moiety from about 40% to about 60% based on the total amount of the biodegradable support scaffold. In some embodiments, the biodegradable support scaffold comprises an amount of hyaluronan or a hyaluronan moiety based on the total amount of the biodegradable support scaffold of about 10%, 15%, 20%, 25%, 30%, 35%, 40%, 45%, 50%, 55%, 60%, 65%, 70%, 75%, 80%, 85% or 90% or a range defined by any two of the preceding values.

In some embodiments, the biodegradable support scaffold comprises a heparin or heparan sulfate. In some embodiments, the biodegradable support scaffold comprises an amount of heparin or heparan sulfate from about 10% to about 90% based on the total amount of the biodegradable support scaffold. In some embodiments, the biodegradable support scaffold comprises an amount of heparin or heparan sulfate from about 10% to about 90% based on the total amount of the biodegradable support scaffold. In some embodiments, the biodegradable support scaffold comprises an amount of heparin or heparan sulfate from about 30% to about 70% based on the total amount of the biodegradable support scaffold. In some embodiments, the biodegradable support scaffold comprises an amount of heparin or heparan sulfate from about 40% to about 60% based on the total amount of the biodegradable support scaffold. In some embodiments, the biodegradable support scaffold comprises an amount of heparin or heparan sulfate moiety based on the total amount of the biodegradable support scaffold of about 10%, 15%, 20%, 25%, 30%, 35%, 40%, 45%, 50%, 55%, 60%, 65%, 70%, 75%, 80%, 85% or 90% or a range defined by any two of the preceding values.

In some embodiments, the biodegradable support scaffold comprises collagen. In some embodiments, the collagen is human collagen. In some embodiments, the collagen is Type-I collagen. In some embodiments, the collagen is Type-III collagen. In some embodiments, the collagen is Type-I collagen, Type-II collagen or Type-III collagen, or any combination thereof. In some embodiments, the biodegradable support scaffold comprises an amount of collagen from about 10% to about 90% based on the total amount of the biodegradable support scaffold. In some embodiments, the biodegradable support scaffold comprises an amount of collagen from about 10% to about 50% based on the total amount of the biodegradable support scaffold. In some embodiments, the biodegradable support scaffold comprises an amount of collagen from about 15% to about 40% based on the total amount of the biodegradable support scaffold. In some embodiments, the biodegradable support scaffold comprises an amount of collagen from about 20% to about 30% based on the total amount of the biodegradable support scaffold. In some embodiments, the biodegradable support scaffold comprises an amount of collagen based on the total amount of the biodegradable support scaffold of about 10%, 15%, 20%, 25%, 30%, 35%, 40%, 45%, 50%, 55%, 60%, 65%, 70%, 75%, 80%, 85% or 90% or a range defined by any two of the preceding values.

In some embodiments, the biodegradable support scaffold comprises polyethylene glycol (PEG) or a PEG moiety. In some embodiments, the biodegradable support scaffold comprises an amount of PEG or a PEG moiety from about 10% to about 90% based on the total amount of the biodegradable support scaffold. In some embodiments, the biodegradable support scaffold comprises an amount of PEG or a PEG moiety from about 10% to about 50% based on the total amount of the biodegradable support scaffold. In some embodiments, the biodegradable support scaffold comprises an amount of PEG or a PEG moiety from about 15% to about 40% based on the total amount of the biodegradable support scaffold. In some embodiments, the biodegradable support scaffold comprises an amount of PEG or a PEG moiety from about 20% to about 30% based on the total amount of the biodegradable support scaffold. In some embodiments, the biodegradable support scaffold comprises an amount of PEG or a PEG moiety based on the total amount of the biodegradable support scaffold of about 0.1%, 0.5%, 1%, 2%, 3%, 4%, 5%, 10%, 15%, 20%, 25%, 30%, 35%, 40%, 45%, 50%, 55%, 60%, 65%, 70%, 75%, 80%, 85% or 90% or a range defined by any two of the preceding values.

In some embodiments, the biodegradable support scaffold comprises disulfide linkages.

In some embodiments, the biodegradable support scaffold comprises a cross-linker. In some embodiments, the biodegradable support scaffold comprises an amount of cross-linker from about 10% to about 50% based on the total amount of the biodegradable support scaffold. In some embodiments, the biodegradable support scaffold comprises an amount of cross-linker from about 15% to about 40% based on the total amount of the biodegradable support scaffold. In some embodiments, the biodegradable support scaffold comprises an amount of cross-linker from about 20% to about 30% based on the total amount of the biodegradable support scaffold. In some embodiments, the biodegradable support scaffold comprises an amount of cross-linker based on the total amount of the biodegradable support scaffold of about 10%, 15%, 20%, 25%, 30%, 35%, 40%, 45%, 50%, 55%, 60%, 65%, 70%, 75%, 80%, 85% or 90% or a range defined by any two of the preceding values. In some embodiments, the cross-linker comprises a PEG moiety.

In some embodiments, a site that is at risk of fibroplasia or characterized by fibroplasia is a site that, upon incision, wounding or other injury, would incur scarring or fibrosis if not treated by the compositions and/or methods provided herein. For example, in some embodiments, a site that is at risk of fibroplasia or characterized by fibroplasia does not include a site that has been pre-treated by IL-10 or other wound healing composition prior to incision, wounding or other injury. While not intending to be bound by the following, it is contemplated that the wound healing process of a site that has been pre-treated by IL-10 or other wound healing composition prior to incision, wounding or other injury, is not the same as the wound healing process when a composition is administered only subsequent to the incision, wounding or other injury. And the present methods and compositions are designed to provide a manner for wound healing that does not require pre-treatment by IL-10 or other wound healing composition prior to incision, wounding or other injury. Some embodiments provide a method for preventing or reducing scarring or process characterized by fibroplasia including but not limited to postsurgical wounds, traumatic wounds, hypertrophic scars, burn contractures, solid organ fibrosis, and intraabdominal adhesions by administering a therapeutically effective amount of IL-10 to a location in a subject for a period of time sufficient to prevent or reduce scarring or fibrosis, said administering comprising a single administration of a composition as disclosed and described herein to an incision or wound site in the subject. Some such embodiments provide a method for preventing or reducing scarring or process characterized by excessive fibroplasia including but not limited to pathologic scars and keloids.

Some embodiments provide a method for preventing or reducing scarring of an incision or wound comprising administering a therapeutically effective amount of IL-10 to a location in a subject for a period of time sufficient to prevent or reduce scarring, said administering comprising a single administration of the composition as disclosed and described herein to an incision or wound site in the subject.

Some embodiments provide a method for preventing or reducing scarring of an incision or wound in a subject, comprising: providing a composition as disclosed and described herein; and introducing the composition to a location in a single administration; and maintaining an amount of IL-10 for a period of time sufficient to prevent or reduce scarring at the location.

In some embodiments, the period of time is at least about 1 day. In some embodiments, the period of time is at least about 2 days. In some embodiments, the period of time is at least about 3 days. In some embodiments, the period of time is at least about 4 days. In some embodiments, the period of time is about 2 to about 30 days. In some embodiments, the period of time is about 3 to about 7 days. In some embodiments, the period of time is at least about 1, 2, 3, 5, 7, 10, 12, 15, 18, 20 or 30 days or a range defined by any two of the preceding values.

Some embodiments provide an extended release biocompatible composition for preventing or reducing scarring in a subject, comprising: a biodegradable support scaffold; and IL-10, wherein the biodegradable support scaffold is configured to release from about 0.015 nM to about 0.015 µM of IL-10 over a period of time to the dermis, epidermis, wound microenvironment, wound tissue homogenate, serum, plasma, or other relevant anatomical site for increased fibrosis.

In some embodiments, the amount of IL-10 in the dermis, epidermis, wound microenvironment, wound tissue homogenate, serum, plasma, or other relevant anatomical site for increased fibrosis is about 0.015 nM, 0.020 nM, 0.025 nM, 0.030 nM, 0.035 nM, 0.040 nM, 0.045 nM, 0.050 nM, 0.055 nM, 0.060 nM, 0.065 nM, 0.070 nM, 0.075 nM, 0.080 nM, 0.085 nM, 0.090 nM, 0.095 nM, 0.100 nM, 0.110 nM, 0.120 nM, 0.130 nM, 0.140 nM, 0.150 nM, 0.160 nM, 0.170 nM, 0.180 nM, 0.190 nM, 0.200 nM, 0.220 nM, 0.240 nM, 0.260 nM, 0.280 nM, 0.300 nM, 0.350 nM, 0.400 nM, 0.450 nM, 0.500 nM, 0.550 nM, 0.600 nM, 0.650 nM, 0.700 nM, 0.750 nM, 0.800 nM, 0.850 nM, 0.900 nM, 0.950 nM, 1.00 nM, 1.10 nM, 1.20 nM, 1.30 nM, 1.40 nM, 1.50 nM, 1.60 nM, 1.70 nM, 1.80 nM, 1.90 nM, 2.00 nM, 2.50 nM, 3.00 nM, 3.50 nM, 0.004 µM, 0.006 µM, 0.008 µM, 0.010 µM, 0.012 µM, 0.014 µM, 0.015 µM, 0.016 µM, 0.017 µM, 0.018 µM, 0.019 µM, 0.020 µM, 0.021 µM, 0.022 µM, 0.023 µM, 0.024 µM, or 0.025 µM, or within a range defined by any two of the preceding values, for the period of time. In some embodiments, the amount of IL-10 is about 0.100 nM, 0.110 nM, 0.120 nM, 0.130 nM, 0.140 nM, 0.150 nM, 0.160 nM, 0.170 nM, 0.180 nM, 0.190 nM, 0.200 nM, 0.220 nM, 0.240 nM, 0.260 nM, 0.280 nM, 0.300 nM, 0.350 nM, 0.400 nM, 0.450 nM, 0.500 nM, 0.550 nM, 0.600 nM, 0.650 nM, 0.700 nM, 0.750 nM, 0.800 nM, 0.850 nM, 0.900 nM, 0.950 nM, 1.00 nM, 1.10 nM, 1.20 nM, 1.30 nM, 1.40 nM, 1.50 nM, 1.60 nM, 1.70 nM, 1.80 nM, 1.90 nM, 2.00 nM, 2.50 nM, 3.00 nM, 3.50 nM, 0.004 µM, 0.006 µM, 0.008 µM, 0.010 µM, 0.012 µM, 0.014 µM, 0.015 µM, 0.016 µM, 0.017 µM, 0.018 µM, 0.019 µM, 0.020 µM, 0.021 µM, 0.022 µM, 0.023 µM, 0.024 µM, or 0.025 µM, or within a range defined by any two of the preceding values, for the period of time. In some embodiments, the amount of IL-10 is about 0.200 nM, 0.220 nM, 0.240 nM, 0.260 nM, 0.280 nM, 0.300 nM, 0.350 nM, 0.400 nM, 0.450 nM, 0.500 nM, 0.550 nM, 0.600 nM, 0.650 nM, 0.700 nM, 0.750 nM, 0.800 nM, 0.850 nM, 0.900 nM, 0.950 nM, 1.00 nM, 1.10 nM, 1.20 nM, 1.30 nM, 1.40 nM, 1.50 nM, 1.60 nM, 1.70 nM, 1.80 nM, 1.90 nM, 2.00 nM, 2.50 nM, 3.00 nM, 3.50 nM, 0.004 µM, 0.006 µM, 0.008 µM, 0.010 µM, 0.012 µM, 0.014 µM, 0.015 µM, 0.016 µM, 0.017 µM, 0.018 µM, 0.019 µM, 0.020 µM, 0.021 µM, 0.022 µM, 0.023 µM, 0.024 µM, or 0.025 µM, or within a range defined by any two of the preceding values, for the period of time. In some embodiments, the amount of IL-10 is about 0.300 nM, 0.350 nM, 0.400 nM, 0.450 nM, 0.500 nM, 0.550 nM, 0.600 nM, 0.650 nM, 0.700 nM, 0.750 nM, 0.800 nM, 0.850 nM, 0.900 nM, 0.950 nM, 1.00 nM, 1.10 nM, 1.20 nM, 1.30 nM, 1.40 nM, 1.50 nM, 1.60 nM, 1.70 nM, 1.80 nM, 1.90 nM, 2.00 nM, 2.50 nM, 3.00 nM, 3.50 nM, 0.004 µM, 0.006 µM, 0.008 µM, 0.010 µM, 0.012 µM, 0.014 µM, 0.015 µM, 0.016 µM, 0.017 µM, 0.018 µM, 0.019 µM, 0.020 µM, 0.021 µM, 0.022 µM, 0.023 µM, 0.024 µM, or 0.025 µM, or within a range defined by any two of the preceding values, for the period of time. In some embodiments, the amount of IL-10 is about 0.400 nM, 0.450 nM, 0.500 nM, 0.550 nM, 0.600 nM, 0.650 nM, 0.700 nM, 0.750 nM, 0.800 nM, 0.850 nM, 0.900 nM, 0.950 nM, 1.00 nM, 1.10 nM, 1.20 nM, 1.30 nM, 1.40 nM, 1.50 nM, 1.60 nM, 1.70 nM, 1.80 nM, 1.90 nM, 2.00 nM, 2.50 nM, 3.00 nM, 3.50 nM, 0.004 µM, 0.006 µM, 0.008 µM, 0.010 µM, 0.012 µM, 0.014 µM, 0.015 µM, 0.016 µM, 0.017 µM, 0.018 µM, 0.019 µM, 0.020 µM, 0.021 µM, 0.022 µM, 0.023 µM, 0.024 µM, or 0.025 µM, or within a range defined by any two of the preceding values, for the period of time. In some embodiments, the amount of IL-10 is about 0.500 nM, 0.550 nM, 0.600 nM, 0.650 nM, 0.700 nM, 0.750 nM, 0.800 nM, 0.850 nM, 0.900 nM, 0.950 nM, 1.00 nM, 1.10 nM, 1.20 nM, 1.30 nM, 1.40 nM, 1.50 nM, 1.60 nM, 1.70 nM, 1.80 nM, 1.90 nM, 2.00 nM, 2.50 nM, 3.00 nM, 3.50 nM, 0.004 µM, 0.006 µM, 0.008 µM, 0.010 µM, 0.012 µM, 0.014 µM, or 0.015 µM for the period of time or within a range defined by any two of the preceding values for the period of time. In some embodiments, the amount of IL-10 is about 0.600 nM, 0.650 nM, 0.700 nM, 0.750 nM, 0.800 nM, 0.850 nM, 0.900 nM, 0.950 nM, 1.00 nM, 1.10 nM, 1.20 nM, 1.30 nM, 1.40 nM, 1.50 nM, 1.60 nM, 1.70 nM, 1.80 nM, 1.90 nM, 2.00 nM, 2.50 nM, 3.00 nM, 3.50 nM, 0.004 µM, 0.006 µM, 0.008 µM, 0.010 µM, 0.012 µM, 0.014 µM, or 0.015 µM for the period of time or within a range defined by any two of the preceding values for the period of time. In some embodiments, the amount of IL-10 is about 0.700 nM, 0.750 nM, 0.800 nM, 0.850 nM, 0.900 nM, 0.950 nM, 1.00 nM, 1.10 nM, 1.20 nM, 1.30 nM, 1.40 nM, 1.50 nM, 1.60 nM, 1.70 nM, 1.80 nM, 1.90 nM, 2.00 nM, 2.50 nM, 3.00 nM, 3.50 nM, 0.004 µM, 0.006 µM, 0.008 µM, 0.010 µM, 0.012 µM, 0.014 µM, or 0.015 µM for the period of time or within a range defined by any two of the preceding values for the period of time. In some embodiments, the amount of IL-10 is about 0.800 nM, 0.850 nM, 0.900 nM, 0.950 nM, 1.00 nM, 1.10 nM, 1.20 nM, 1.30 nM, 1.40 nM, 1.50 nM, 1.60 nM, 1.70 nM, 1.80 nM, 1.90 nM, 2.00 nM, 2.50 nM, 3.00 nM, 3.50 nM, 0.004 µM, 0.006 µM, 0.008 µM, 0.010 µM, 0.012 µM, 0.014 µM, or 0.015 µM for the period of time or within a range defined by any two of the preceding values for the period of time. In some embodiments, the amount of IL-10 is about 0.900 nM, 0.950 nM, 1.00 nM, 1.10 nM, 1.20 nM, 1.30 nM, 1.40 nM, 1.50 nM, 1.60 nM, 1.70 nM, 1.80 nM, 1.90 nM, 2.00 nM, 2.50 nM, 3.00 nM, 3.50 nM, 0.004 µM, 0.006 µM, 0.008 µM, 0.010 µM, 0.012 µM, 0.014 µM, or 0.015 µM for the period of time or within a range defined by any two of the preceding values for the period of time. In some embodiments, the amount of IL-10 is about 1.00 nM, 1.10 nM, 1.20 nM, 1.30 nM, 1.40 nM, 1.50 nM, 1.60 nM, 1.70 nM, 1.80 nM, 1.90 nM, 2.00 nM, 2.50 nM, 3.00 nM, 3.50 nM, 0.004 µM, 0.006 µM, 0.008 µM, 0.010 µM, 0.012 µM, 0.014 µM, or 0.015 M for the period of time or within a range defined by any two of the preceding values for the period of time. In some embodiments, the amount of IL-10 is about 2.00 nM, 2.50 nM, 3.00 nM, 3.50 nM, 0.004 µM, 0.006 µM, 0.008 µM, 0.010 µM, 0.012 µM, 0.014 µM, or 0.015 µM for the period of time or within a range defined by any two of the preceding values for the period of time. In some embodiments, the amount of IL-10 is about 3.00 nM, 3.50 nM, 0.004 µM, 0.006 µM, 0.008 µM, 0.010 µM, 0.012 µM, 0.014 µM, or 0.015 µM for the period of time or within a range defined by any two of the preceding values for the period of time. In some embodiments, the amount of IL-10 is about 0.004 µM, 0.006 µM, 0.008 µM, 0.010 µM, 0.012 µM, 0.014 µM, or 0.015 µM for the period of time or within a range defined by any two of the preceding values for the period of time. In some embodiments, the amount of IL-10 in the dermis, epidermis, wound microenvironment, wound tissue homogenate, serum, plasma, or other relevant anatomical site for increased fibrosis is from about 0.015 nM, 0.020 nM, 0.025 nM, 0.030 nM, 0.035 nM, 0.040 nM, 0.045 nM, 0.050 nM, 0.055 nM, 0.060 nM, 0.065 nM, 0.070 nM, 0.075 nM, 0.080 nM, 0.085 nM, 0.090 nM, 0.095 nM, 0.100 nM, 0.110 nM, 0.120 nM, 0.130 nM, 0.140 nM, 0.150 nM, 0.160 nM, 0.170 nM, 0.180 nM, 0.190 nM, 0.200 nM, 0.220 nM, 0.240 nM, 0.260 nM, 0.280 nM, 0.300 nM, 0.350 nM, 0.400 nM, 0.450 nM, 0.500 nM, 0.550 nM, 0.600 nM, 0.650 nM, 0.700 nM, 0.750 nM, 0.800 nM, 0.850 nM, 0.900 nM, 0.950 nM, 1.00 nM, 1.10 nM, 1.20 nM, 1.30 nM, 1.40 nM, 1.50 nM, 1.60 nM, 1.70 nM, 1.80 nM, 1.90 nM, or 2.00 nM, or within a range defined by any two of the preceding values, for the period of time. In some embodiments, the amount of IL-10 in the dermis, epidermis, wound microenvironment, wound tissue homogenate, serum, plasma, or other relevant anatomical site for increased fibrosis is from about 0.015 nM, 0.020 nM, 0.025 nM, 0.030 nM, 0.035 nM, 0.040 nM, 0.045 nM, 0.050 nM, 0.055 nM, 0.060 nM, 0.065 nM, 0.070 nM, 0.075 nM, 0.080 nM, 0.085 nM, 0.090 nM, 0.095 nM, 0.100 nM, 0.110 nM, 0.120 nM, 0.130 nM, 0.140 nM, 0.150 nM, 0.160 nM, 0.170 nM, 0.180 nM, 0.190 nM, 0.200 nM, 0.220 nM, 0.240 nM, 0.260 nM, 0.280 nM, 0.300 nM, 0.350 nM, 0.400 nM, 0.450 nM, 0.500 nM, 0.550 nM, 0.600 nM, 0.650 nM, 0.700 nM, 0.750 nM, 0.800 nM, 0.850 nM, 0.900 nM, 0.950 nM, or 1.00 nM, or within a range defined by any two of the preceding values, for the period of time. In some embodiments, the amount of IL-10 in the dermis, epidermis, wound microenvironment, wound tissue homogenate, serum, plasma, or other relevant anatomical site for increased fibrosis is from about 0.015 nM, 0.020 nM, 0.025 nM, 0.030 nM, 0.035 nM, 0.040 nM, 0.045 nM, 0.050 nM, 0.055 nM, 0.060 nM, 0.065 nM, 0.070 nM, 0.075 nM, 0.080 nM, 0.085 nM, 0.090 nM, 0.095 nM, 0.100 nM, 0.110 nM, 0.120 nM, 0.130 nM, 0.140 nM, 0.150 nM, 0.160 nM, 0.170 nM, 0.180 nM, 0.190 nM, 0.200 nM, 0.220 nM, 0.240 nM, 0.260 nM, 0.280 nM, 0.300 nM, 0.350 nM, 0.400 nM, 0.450 nM, or 0.500 nM, or within a range defined by any two of the preceding values, for the period of time. In some embodiments, the amount of IL-10 in the dermis, epidermis, wound microenvironment, wound tissue homogenate, serum, plasma, or other relevant anatomical site for increased fibrosis is from about 0.015 nM, 0.020 nM, 0.025 nM, 0.030 nM, 0.035 nM, 0.040 nM, 0.045 nM, 0.050 nM, 0.055 nM, 0.060 nM, 0.065 nM, 0.070 nM, 0.075 nM, 0.080 nM, 0.085 nM, 0.090 nM, 0.095 nM, 0.100 nM, 0.110 nM, 0.120 nM, 0.130 nM, 0.140 nM, 0.150 nM, 0.160 nM, 0.170 nM, 0.180 nM, 0.190 nM, or 0.200 nM, or within a range defined by any two of the preceding values, for the period of time. In some embodiments, the period of time may be measured starting from initial administration of the composition. In some embodiments, the period of time is up to about 0.5, 1, 2, 3, 4, 5, 6, 7, 8, 9, 10, 12, 15, 20, 25 or 30 days or up to a number that falls within a range defined by any two of the preceding values. In some embodiments, the period of time may be the first seven days after administration of IL-10. In some embodiments, the period of time may be the first 5 days after administration of IL-10. In some embodiments, the period of time may be the first three days after administration of IL-10.

In some embodiments, the amount of IL-10 in the dermis, epidermis, wound microenvironment, wound tissue homogenate, serum, plasma, or other relevant anatomical site for increased fibrosis is from about 0.015 nM to 0.015 µM for a sustained release time period. In some embodiments, the amount of IL-10 is about 0.015 nM, 0.04 nM, 0.08 nM, 0.12 nM, 0.16 nM, or 0.2 nM, or within a range defined by any two of the preceding values, for the sustained release time period. In some embodiments, the sustained release time period may be measure starting from initial administration of the composition. In some embodiments, the sustained release time period is up to about 1, 2, 3, 5, 7, 10, 12, 15, 18, 20 or 30 days or a range defined by any two of the preceding values. In some embodiments, the sustained release time period may be up to seven days after administration. In some embodiments, the sustained release time period may be from 1 day to up to 14 days after administration of IL-10. In some embodiments, the sustained release time period may be from 2 days to up to 14 days after administration of IL-10. In some embodiments, the sustained release time period may be from 2 days to up to seven days after administration of IL-10. In some embodiments, the sustained release time period may be from after the first day to up to seven days after administration of IL-10.

In some embodiments, the amount of IL-10 in the dermis, epidermis, wound microenvironment, wound tissue homogenate, serum, plasma, or other relevant anatomical site for increased fibrosis is from about 0.002 µM to 0.015 µM for a bolus time period and between 0.015 nM to about 0.2 nM for a sustained release time period. In some embodiments, the amount of IL-10 is about 0.002 µM, 0.004 µM, 0.006 µM, 0.008 µM, 0.010 µM, 0.012 µM, 0.014 µM, or 0.015 µM for the bolus time period or within a range defined by any two of the preceding values for the bolus time period. In some embodiments, the amount of IL-10 is about 0.015 nM, 0.04 nM, 0.08 nM, 0.12 nM, 0.16 nM, or 0.2 nM for the sustained release time period or within a range defined by any two of the preceding values for the sustained release time period. In some embodiments, the bolus time period may be measured starting from initial administration of the composition. In some embodiments, the sustained release time period may be measure starting from initial administration of the composition. In some embodiments, the bolus time period is up to about 0.5, 1, 2, 3, 5, or 7 days or up to a number that falls within a range defined by any two of the preceding values. In some embodiments, the sustained release time period is up to about 1, 2, 3, 5, 7, 10, 12, 15, 18, 20 or 30 days or a range defined by any two of the preceding values. In some embodiments, the maximum concentration of IL-10 during the bolus time period may be greater than the maximum concentration of IL-10 during the sustained release time. In some embodiments, the bolus time period may be the first three days after administration of IL-10. In some embodiments, the bolus time period may be the first two days after administration of IL-10. In some embodiments, the sustained release time period may be up to seven days after administration. In some embodiments, the sustained release time period may be from 1 day to up to 14 days after administration of IL-10. In some embodiments, the sustained release time period may be from 2 days to up to 14 days after administration of IL-10. In some embodiments, the sustained release time period may be from 2 days to up to seven days after administration of IL-10. In some embodiments, the bolus time period may be the first day after administration of IL-10 and the sustained release time period may be from after the first day to up to seven days after administration of IL-10.

The biocompatible compositions provided herein comprise IL-10. In some embodiments, the amount of IL-10 in the composition is from about 0.017 µM to about 0.035 µM. In some embodiments, the amount of IL-10 in the composition is about 0.017 µM, 0.019 µM, 0.021 µM, 0.023 µM, 0.025 µM, 0.027 µM, 0.029 µM, 0.031 µM, 0.033 µM, or 0.055 µM, or within a range defined by any two of the preceding values.

In some embodiments, the incision or wound site is at a dermal layer or epidermis or other relevant anatomical site for increased fibrosis.

In some embodiments, the incision or wound site includes a dermal layer or epidermis or other relevant anatomical site for increased fibrosis.

In some embodiments, the wound is restored to a condition substantially identical to the surrounding tissue within a second period of time from initial administration of the composition. In some embodiments, the second period of time is at least about 1 day. In some embodiments, the second period of time is at least about 2 days. In some embodiments, the second period of time is at least about 3 days. In some embodiments, the second period of time is at least about 4 days. In some embodiments, the second period of time is about 2 to about 30 days. In some embodiments, the second period of time is about 3 to about 7 days. In some embodiments, the second period of time is at least about 1, 2, 3, 5, 7, 10, 12, 15, 18, 20 or 30 days or a range defined by any two of the preceding values.

In some embodiments, the wound is a trauma wound, and the composition is administered at the wound site within a third period of time from initial wound formation. In some embodiments, the third period of time is within about 1 minute. In some embodiments, the third period of time is within about 5 minutes. In some embodiments, the third period of time is within about 30 minutes. In some embodiments, the third period of time is within about 1 hour. In some embodiments, the third period of is within about 2 hours. In some embodiments, the third period of is within about 4 hours. In some embodiments, the third period of is within about 6 hours. In some embodiments, the third period of is within about 12 hours. In some embodiments, the third period of is within about 24 hours. In some embodiments, the third period of time is within about 1 minute, 5 minutes, 30 minutes, 60 minutes, 2 hours, 4 hours, 6 hours, or 24 hours or within a range defined by any two of the preceding values.

In some embodiments, the wound may be a hypertrophic scar, keloid, burn contracture, and the composition is administered at the wound site within a third period of time from initial wound formation. In some embodiments, the third period of time is within about 5 minutes. In some embodiments, the third period of time is within about 30 minutes. In some embodiments, the third period of time is within about 1 hour. In some embodiments, the third period of time is within about 2 hours. In some embodiments, the third period of time is within about 4 hours. In some embodiments, the third period of time is within about 6 hours. In some embodiments, the third period of time is within about 12 hours. In some embodiments, the third period of time is within about 24 hours. In some embodiments, the third period of time is within about 1 minute, 5 minutes, 30 minutes, 60 minutes, 2 hours, 4 hours, 6 hours, or 24 hours or within a range defined by any two of the preceding values.

In some embodiments, the area of application is an anatomic specific area, such as the intraabdominal cavity for adhesions, the kidney, lung or liver for organ specific fibrosis, and the composition is administered at the site of fibroplasia within a third period of time from initial scar formation. In some embodiments, the third period of time is within about 5 minutes. In some embodiments, the third period of time is within about 30 minutes. In some embodiments, the third period of time is within about 1 hour. In some embodiments, the third period of time is within about 2 hours. In some embodiments, the third period of time is within about 4 hours. In some embodiments, the third period of time is within about 6 hours. In some embodiments, the third period of is within about 12 hours. In some embodiments, the third period of time is within about 24 hours. In some embodiments, the third period of time is within about 1 minute, 5 minutes, 30 minutes, 60 minutes, 2 hours, 4 hours, 6 hours, or 24 hours or within a range defined by any two of the preceding values. Some such embodiments provide a method for preventing or reducing scarring or process characterized by excessive fibroplasia including but not limited to pathologic scars and keloids.

In some embodiments, the method further comprises making a surgical incision, wherein the composition is administered at the incision.

Some embodiments provide a method of evaluating a composition for treating a wound including: providing a dosage of the composition to a wound in a statistically relevant number of animals; and evaluating the wound in each animal after a period of time using an Assessment Scale value to obtain an Assessment Scale score, wherein said Assessment Scale score is based on the measurement of at least 2 parameters selected from the group consisting of i) the quantification of topography, ii) epidermal height, and iii) the nuclear orientation of the basal keratinocytes in the epidermis; and iv) the quantification of the scar area, v) dermal appendages, and vi) vascularity (vessel density) in the dermis of the scars. In some embodiments, each parameter is calculated to provide an Assessment Scale value (INDEX), wherein an Assessment Scale score is calculated by ("Σ INDEX/n)×100 where n is the number of parameters being evaluated. In some embodiments, the animals are mice. In some embodiments, the statistically relevant number is three or more. In some embodiments, the period of time is 20 days. In some embodiments, the dosage is a single dosage. In some embodiments, the composition comprises IL-10. In some embodiments, the composition comprises IL-10 and a biodegradable support scaffold. In some embodiments, n is 2, 3, 4, 5 or 6. In some embodiments, n is 3. In some embodiments, n is 4. In some embodiments, n is 5. In some embodiments, n is 6.

Compositions

Some embodiments provide an extended release biocompatible composition for preventing or reducing scarring of an incision or wound site in a subject, comprising: a biodegradable support scaffold; and IL-10, wherein the amount of IL-10 in the composition is from about 0.05 ng/µL to about 1500 ng/µL. In some embodiments, the composition may be a hydrogel.

In some embodiments, the amount of IL-10 in the composition is from about 1 ng/µL to about 1000 ng/µL. In some embodiments, the amount of IL-10 in the composition is from about 2 ng/µL to about 500 ng/µL. In some embodiments, the amount of IL-10 in the composition is from about 4 ng/µL to about 250 ng/mL. In some embodiments, the amount of IL-10 in the composition is from about 6 ng/µL to about 125 ng/µL. In some embodiments, the amount of IL-10 in the composition is from about 8 ng/µL to about 100 ng/µL. In some embodiments, the amount of IL-10 in the composition is from about 10 ng/µL to about 75 ng/µL. In some embodiments, the amount of IL-10 in the composition is from about 20 ng/µL to about 45 ng/µL.

In some embodiments, the amount of IL-10 in the composition is from about 5 ng to about 5000 ng. In some embodiments, the amount of IL-10 in the composition is from about 50 ng to about 2500 ng. In some embodiments, the amount of IL-10 in the composition is from about 100 ng to about 1250 ng.

In some embodiments, the composition is from about 0.1 mg to about 1 g. In some embodiments, the composition is from about 0.1 mg to about 500 mg. In some embodiments, the composition is from about 0.1 mg to about 250 mg. In some embodiments, the composition is from about 0.1 mg to about 125 mg. In some embodiments, the composition is from about 0.1 mg to about 80 mg. In some embodiments, the composition is from about 0.1 mg to about 40 mg. In some embodiments, the composition is from about 0.1 mg to about 20 mg.

The daily dosage of IL-10 may be varied over a wide range; e.g., from about 0.1 µg to about 10,000 µg per adult human per day.

Therapeutically effective dosages of IL-10 can range from 0.1 µg to about 0.5 µg per dose, from about 0.5 µg to about 1.0 µg per dose, from about 1.0 µg per dose to about 5.0 µg per dose, from about 5.0 µg to about 10 µg per dose, from about 10 µg to about 20 µg per dose, from about 20 µg per dose to about 30 µg per dose, from about 30 µg per dose to about 40 µg per dose, from about 40 µg per dose to about 50 µg per dose, from about 50 µg per dose to about 60 µg per dose, from about 60 µg per dose to about 70 µg per dose, from about 70 µg to about 80 µg per dose, from about 80 µg per dose to about 100 µg per dose, from about 100 µg to about 150 µg per dose, from about 150 µg to about 200 µg per dose, from about 200 µg per dose to about 250 µg per dose, from about 250 µg to about 300 µg per dose, from about 300 µg to about 400 µg per dose, from about 400 µg to about 500 µg per dose, from about 500 µg to about 600 µg per dose, from about 600 µg to about 700 µg per dose, from about 700 µg to about 800 µg per dose, from about 800 µg to about 900 µg per dose, from about 900 µg to about 1000 µg per dose, from about 1 mg to about 10 mg per dose. An effective amount of IL-10 is ordinarily supplied at a dosage level of from about 0.01 mg/cm$^2$ to about 150 mg/cm$^2$ per day. Typically, the range is from about 0.1 to about 80 mg/cm$^2$ per day, and especially from about 0.2 mg/cm$^2$ to about 40 mg/cm$^2$ per day. In some embodiments, the composition may be administered on a regimen of about 1 to about 10 times per day, or continuous infusion for a period of from about 1, 5, 10, 15, 30 or 60 minutes, or 1, 2, 3, 5, 7, 10, 12, 15, 18, 20 or 24 hours or a range defined by any two of the preceding values. In a typical embodiment, the composition may be administered once.

Some embodiments provide an extended release biocompatible composition comprising from about 1 mg/mL to about 300 mg/mL IL-10 having from about 15% release to about 50% release of IL-10 relative to the initial amount of IL-10 in the initial composition within 24 hours of initial administration. In some embodiments the extended release biocompatible composition comprising from about 1 mg/mL to about 300 mg/mL IL-10 may have about 5%, 10%, 15%, 20%, 25%, 30%, 35%, 40%, 45% or 50%, or within a range defined by any two of the preceding values, release of IL-10 relative to the initial amount of IL-10 in the initial composition within 24 hours of initial administration. In some embodiments the extended release biocompatible composition comprising from about 1 mg/mL to about 300 mg/mL IL-10 may have 0.1%, 0.2%, 0.4%, 0.8%, 1.2%, 1.6%, 2%, 2.4%, 2.8%, 3.2%, 3.6%, 4.0%, 4.4%, 4.8%, 5.2%, 5.6%, 6.0%, 6.4%, 6.8%, 7.2%, 7.6%, 8.0%, 8.4%, 8.8%, 9.2%, 9.6%, or 10%, or within a range defined by any two of the preceding values, release of IL-10 relative to the initial amount of IL-10 in the initial composition from the time period of about 24 hours to about 48 hours of initial administration. In some embodiments the extended release biocompatible composition comprising from about 1 mg/mL to about 300 mg/mL IL-10 may have 0.01%, 0.02%, 0.04%, 0.08%, 0.12%, 0.16%, 0.2%, 0.24%, 0.28%, 0.32%, 0.36%, 0.40%, 0.44%, 0.48%, 0.52%, 0.56%, 0.6%, 0.64%, 0.68%, 0.72%, 0.76%, 0.80%, 0.84%, 0.88%, 0.92%, 0.96%, or 1.0%, or within a range defined by any two of the preceding values, release of IL-10 relative to the initial amount of IL-10 in the initial composition from the time period of about 48 hours to about 72 hours of initial administration. In some embodiments the extended release biocompatible composition comprising from about 1 mg/mL to about 300 mg/mL IL-10 may have 0.001%, 0.002%, 0.004%, 0.008%, 0.012%, 0.016%, 0.02%, 0.024%, 0.028%, 0.032%, 0.036%, 0.040%, 0.044%, 0.048%, 0.052%, 0.056%, 0.06%, 0.064%, 0.068%, 0.072%, 0.076%, 0.080%, 0.084%, 0.088%, 0.092%, 0.096%, 0.1%, 0.12%, 0.16%, 0.2%, 0.24%, 0.28%, 0.32%, 0.36%, 0.40%, 0.44%, 0.48%, 0.52%, 0.56%, 0.6%, 0.64%, 0.68%, 0.72%, 0.76%, 0.80%, 0.84%, 0.88%, 0.92%, 0.96%, or 1.0%, or within a range defined by any two of the preceding values, release of IL-10 relative to the initial amount of IL-10 in the initial composition from the time period of about 72 hours to about 96 hours of initial administration. In some embodiments the extended release biocompatible composition comprising from about 1 mg/mL to about 300 mg/mL IL-10 may have 0.001%, 0.002%, 0.004%, 0.008%, 0.012%, 0.016%, 0.02%, 0.024%, 0.028%, 0.032%, 0.036%, 0.040%, 0.044%, 0.048%, 0.052%, 0.056%, 0.06%, 0.064%, 0.068%, 0.072%, 0.076%, 0.080%, 0.084%, 0.088%, 0.092%, 0.096%, 0.1%, 0.12%, 0.16%, 0.2%, 0.24%, 0.28%, 0.32%, 0.36%, 0.40%, 0.44%, 0.48%, 0.52%, 0.56%, 0.6%, 0.64%, 0.68%, 0.72%, 0.76%, 0.80%, 0.84%, 0.88%, 0.92%, 0.96%, or 1.0%, or within a range defined by any two of the preceding values, release of IL-10 relative to the initial amount of IL-10 in the initial composition from the time period of about 96 hours to about 120 hours of initial administration. In some embodiments the extended release biocompatible composition comprising from about 1 mg/mL to about 300 mg/mL IL-10 may have 0.001%, 0.002%, 0.004%, 0.008%, 0.012%, 0.016%, 0.02%, 0.024%, 0.028%, 0.032%, 0.036%, 0.040%, 0.044%, 0.048%, 0.052%, 0.056%, 0.06%, 0.064%, 0.068%, 0.072%, 0.076%, 0.080%, 0.084%, 0.088%, 0.092%, 0.096%, 0.1%, 0.12%, 0.16%, 0.2%, 0.24%, 0.28%, 0.32%, 0.36%, 0.40%, 0.44%, 0.48%, 0.52%, 0.56%, 0.6%, 0.64%, 0.68%, 0.72%, 0.76%, 0.80%, 0.84%, 0.88%, 0.92%, 0.96%, or 1.0%, or within a range defined by any two of the preceding values, release of IL-10 relative to the initial amount of IL-10 in the initial composition from the time period of about 120 hours to about 144 hours of initial administration. In some embodiments the extended release biocompatible composition comprising from about 1 mg/mL to about 300 mg/mL IL-10 may have 0.001%, 0.002%, 0.004%, 0.008%, 0.012%, 0.016%, 0.02%, 0.024%, 0.028%, 0.032%, 0.036%, 0.040%, 0.044%, 0.048%, 0.052%, 0.056%, 0.06%, 0.064%, 0.068%, 0.072%, 0.076%, 0.080%, 0.084%, 0.088%, 0.092%, 0.096%, 0.1%, 0.12%, 0.16%, 0.2%, 0.24%, 0.28%, 0.32%, 0.36%, 0.40%, 0.44%, 0.48%, 0.52%, 0.56%, 0.6%, 0.64%, 0.68%, 0.72%, 0.76%, 0.80%, 0.84%, 0.88%, 0.92%, 0.96%, or 1.0%, or within a range defined by any two of the preceding values, release of IL-10 relative to the initial amount of IL-10 in the initial composition from the time period of about 144 hours to about 168 hours of initial administration. In some embodiments the amount of IL-10 released within a time period may be established using the following protocol:

Protocol A

Extracel-HP™ HMW-HA hydrogel (Glycosan a division of BioTime, Inc., Alameda, Calif.) including heparin and IL-10 (800 ng in 25 µL for in each well of a 48-well dish) is placed in media (250 µL) such as Dulbecco's Modified Eagle Medium (Life Technologies Corporation, Carlsbad, Calif.). After around 24 hours the media from each well is removed and separately maintained for analysis. Fresh media (250 µL) is added to each well. The amount of IL-10 in each well is measured by ELISA. This process is repeated every 24 hours for a total of seven days. In some embodiments, the composition can have, for example, 25 percent release of IL-10 within 24 hours evaluated using PROTOCOL A, 50 percent release of IL-10 within 48 hours evaluated using PROTOCOL A, 75 percent release of IL-10 within 72 hours evaluated using PROTOCOL A.

In some embodiments, the composition may include a biodegradable support scaffold including at least one of hyaluronan, a hyaluronan moiety, heparin, heparan sulfate, collagen, PEG, a PEG moiety or a cross-linker, as described herein. In some embodiments, the composition may include a biodegradable support scaffold including at least two of hyaluronan, a hyaluronan moiety, heparin, heparan sulfate, collagen, PEG, a PEG moiety or a cross-linker. In some embodiments, the composition may include a biodegradable support scaffold including at least three of hyaluronan, a hyaluronan moiety, heparin, heparan sulfate, collagen, PEG, a PEG moiety or a cross-linker. In some embodiments, the composition may include a biodegradable support scaffold including at least four of hyaluronan, a hyaluronan moiety, heparin, heparan sulfate, collagen, PEG, a PEG moiety or a cross-linker. In some embodiments, the composition may be a hydrogel.

The composition can be formulated readily, for example, by combining the biodegradable support scaffold with any suitable pharmaceutically acceptable excipient for example, but not limited to, binders, diluents, disintegrants, lubricants, fillers, carriers, and the like, as set forth below. Such compositions can be prepared for storage and for subsequent processing.

Acceptable excipients for therapeutic use are well known in the pharmaceutical art, and are described, for example, in Handbook of Pharmaceutical Excipients, 5th edition (Raymond C Rowe, Paul J Sheskey and Siân C Owen, eds. 2005), and Remington: The Science and Practice of Pharmacy, 21st edition (Lippincott Williams & Wilkins, 2005), each of which is hereby incorporated in its entirety. The term "carrier" material or "excipient" herein can mean any substance, not itself a therapeutic agent, used as a carrier and/or diluent and/or adjuvant, or vehicle for delivery of a therapeutic agent to a subject or added to a pharmaceutical composition to improve its handling or storage properties or to permit or facilitate formation of a dose unit of the composition into a gel, lotion, cream, ointment, solid, semi-solid, or a discrete article such as a capsule, tablet, film coated tablet, caplet, gel cap, pill, pellet, bead, and the like. In some embodiments, the composition may be a hydrogel. Excipients can include, by way of illustration and not limitation, diluents, disintegrants, binding agents, wetting agents, polymers, lubricants, glidants, substances added to mask or counteract a disagreeable taste or odor, flavors, colorants, fragrances, and substances added to improve appearance of the composition.

Acceptable excipients include, for example, but are not limited to, lactose, sucrose, starch powder, maize starch or derivatives thereof, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinyl-pyrrolidone, and/or polyvinyl alcohol, saline, dextrose, mannitol, lactose, lecithin, albumin, sodium glutamate, cysteine hydrochloride, and the like. Suitable excipients for the preparation of solutions and syrups include, without limitation, water, polyols, sucrose, invert sugar and glucose.

Any of the foregoing mixtures can be appropriate in treatments and therapies in accordance with the embodiments disclosed herein, provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol. Pharmacol. 32(2):210-8 (2000), Charman W N "Lipids, lipophilic drugs, and oral drug delivery-some emerging concepts." J Pharm Sci 0.89(8): 967-78 (2000), and the citations therein for additional information related to formulations, excipients and carriers well known to pharmaceutical chemists.

In some embodiments, one or more, or any combination of the listed excipients can be specifically included or excluded from the formulations and/or methods disclosed herein.

In some embodiments, the formulation can be in form suitable for bolus administration.

As will be appreciated by those of skill in the art, the amounts of excipients will be determined by drug dosage and dosage form size. In some embodiments, the dosage form size of the composition is in the range of about 5 µL to about 1 liter. This dosage form weight is arbitrary and one skilled in the art will realize that a range of weights can be made and are encompassed. The preferred dosage form size of the composition is 500 µL to 10 mL, more preferably 750 µL to 5 mL, more preferably 1 mL to 5 mL, with the preferred dosage form being a viscous solution.

Methods of Administration

In any of the embodiments, administration can be by bolus administration, e.g., subcutaneous bolus administration, intramuscular bolus administration, intradermal bolus administration and the like. In any of the embodiments, administration can be by infusion, e.g., subcutaneous infusion, intramuscular infusion, intradermal infusion, and the like. In some embodiments, administration can be by direct tissue injections. In some embodiments, the composition may include a hydrogel.

Administration, preferably intradermal administration, of a pharmaceutical composition including a sustained release formulation as disclosed and described herein is accomplished using standard methods and devices, e.g., pens, injector systems, needle and syringe, an intradermal injection system, and the like. In some embodiments, intradermal administration can be achieved by bolus delivery by needle and syringe. In some embodiments, the composition may be a viscous gel, liquid, settable liquid, or semi-solid. In some embodiments, the composition may include a hydrogel. In some embodiments, the settable liquid may set to afford a solid or semi-solid upon administration to the wound.

Solutions or suspensions used for parenteral, intradermal, subcutaneous, intramuscular or topical application can include any of the following components: a sterile diluent, such as water for injection, saline solution, fixed oil, polyethylene glycol, glycerine, propylene glycol or other synthetic solvent; antimicrobial agents, such as benzyl alcohol and methyl parabens; antioxidants, such as ascorbic acid and sodium bisulfite; cheating agents, such as ethylenediaminetetraacetic acid (EDTA); buffers, such as acetates, citrates and phosphates; and agents for the adjustment of tonicity, including, but not limited to sodium chloride, calcium chloride, magnesium chloride, dextrose, glycerol or boric acid. Parenteral preparations can be enclosed in ampoules, disposable syringes or single or multiple dose vials made of glass, plastic or other suitable material.

Parenteral administration of a pharmaceutical compositions including a sustained release formulation as disclosed and described herein, generally characterized by injection, either subcutaneously, intradermally, or intramuscularly is also contemplated herein. In some embodiments, parenteral administration of a pharmaceutical compositions including a sustained release formulation as disclosed and described herein includes direct tissue injections. Injectables can be prepared in conventional forms, either as liquid solutions or suspensions; solid forms suitable for solution or suspension in liquid prior to injection, or as emulsions. Suitable excipients are, for example, water, saline, dextrose, glycerol or ethanol. In addition, if desired, the pharmaceutical compositions to be administered can also contain minor amounts of non-toxic auxiliary substances such as wetting or emulsifying agents, pH buffering agents, stabilizers, solubility enhancers, and other such agents, such as, for example, sodium acetate, sorbitan monolaurate, triethanolamine oleate and cyclodextrins.

Parenteral administration of the compositions includes subcutaneous intramuscular, and intradermal administrations. In some embodiments, parenteral administration of the compositions includes direct tissue injections. Preparations for parenteral administration include sterile solutions ready for injection, sterile dry soluble products, such as lyophilized powders, ready to be combined with a solvent or sterile solution just prior to use, including hypodermic tablets, sterile suspensions ready for injection, sterile dry insoluble products ready to be combined with a vehicle just prior to use and sterile emulsions. In some embodiments, the solutions can be either aqueous or nonaqueous.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thiomersal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEEN® 80). A sequestering or chelating agent of metal ions includes EDTA. Pharmaceutical carriers also include ethyl alcohol, polyethylene glycol and propylene glycol for water miscible vehicles and sodium hydroxide, hydrochloric acid, citric acid or lactic acid for pH adjustment.

The concentration of the IL-10 can be adjusted so that administration, e.g., an injection or infusion, provides an effective amount to produce the desired pharmacological effect. The exact dose depends on the age, weight and condition of the patient or animal as is known in the art.

The unit-dose parenteral preparations can be packaged in container, for example, an ampoule, a vial or a syringe with a needle. All preparations for parenteral administration must be sterile, as is known and practiced in the art.

Illustratively, subcutaneous infusion of a sterile aqueous solution containing an active compound is an effective mode of administration. Another embodiment is a sterile aqueous or oily solution or suspension containing an active material injected as necessary to produce the desired pharmacological effect.

Injectables are typically designed for local administration. Typically a therapeutically effective dosage is formulated to contain a concentration of at least about 0.01% w/w up to about 4% w/w or more, preferably more than 0.1% w/w of the active compound to the treated tissue(s). It is to be further understood that for any particular subject, specific dosage regimens should be adjusted over time according to the individual need and the professional judgment of the person administering or supervising the administration of the formulations, and that the concentration ranges set forth herein are exemplary only and are not intended to limit the scope or practice of the claimed formulations.

The compositions provided herein can be formulated for parenteral administration, e.g., by bolus administration or continuous infusion. Formulations for administration can be presented in unit dosage form, e.g., in ampoules or in multi-dose containers, optionally with an added preservative. The compositions can be suspensions, solutions or emulsions in oily or aqueous vehicles, and can contain formulatory agents such as suspending, stabilizing and/or dispersing agents. Alternatively, the active ingredient can be in powder form for reconstitution with a suitable vehicle, e.g., sterile pyrogen-free water or other solvents, before use.

Some embodiments also include pharmaceutical formulations for parenteral administration, e.g., by bolus administration or continuous infusion, include aqueous suspensions of a hydrogel, having encapsulated therein IL-10. Additionally, suspensions of the hydrogel may be prepared as appropriate. Formulations for administration may be presented in unit dosage form, e.g., in ampoules or in multi-dose containers, with an added preservative. The formulations may take such forms as suspensions, solutions or emulsions in oily or aqueous vehicles, and may contain formulatory agents such as suspending, stabilizing and/or dispersing agents. In some embodiments the formulation can be administered by subcutaneous injection.

The effective daily dosage of the therapeutic agent may be varied over a wide range; e.g., from about 0.05 pg to about 10,000 ng per adult human per day.

Some embodiments provide a method of administering IL-10 to a subject, once about every 5, 10, 12, 15, 20 or 24 hrs. In some embodiments, the IL-10 is administered to a subject at least 1, 2, 3, 4, 5, 6, 8, or 12 times daily.

Methods of Treatment

Some embodiments relate to a method for treating a wound with an extended release biocompatible composition as disclosed and described herein. In some embodiments, the composition may be a hydrogel.

In some embodiments, the wound may be formed by an incision during a surgical procedure. In some embodiments, the wound can be caused by a clean, sharp-edged object such as a knife, scalpel or a razor.

In some embodiments, the wound can be an open type trauma wound. In some aspects, the open type trauma wound can be a severe trauma wound; for example, gunshot wounds, improvised explosive device (IED) wounds, mortar attack wounds, missile attack wounds, rocket propelled grenade (RPG) wounds, grenade wounds, bomb wounds, land mine wounds, and any military or improvised ordinance wounds.

In some embodiments, the wound can be contacted with the extended release biocompatible composition and a dressing. In some aspects, the dressing can be bound to the skin, forming a barrier to prevent further bleeding or oozing of bodily fluids. In some aspects, the dressing can be a surgical dressing. In some aspects, the dressing can be a field wound dressing.

In some embodiments, the wound may be torn, cut or punctured skin.

In some embodiments, the wound may be a penetrating wound. Penetrating wounds can be classified into a number of different types, according to the object that caused the wound. The types of penetrating wounds that can be treated with the present formulations can include, but are not limited to, Incisions or incised wounds—caused by a clean, sharp-edged object such as a knife, scalpel, a razor or a glass splinter;

Lacerations—irregular wounds caused by a blunt impact to soft tissue which lies over hard tissue (e.g. laceration of the skin covering the skull) or tearing of skin and other tissues;

Puncture wounds—caused by an object puncturing the skin, such as a nail, knife, or bullet.

Gunshot wounds—caused by a bullet or similar projectile driving into or through the body. There may be two wounds, one at the site of entry and one at the site of exit;

Improvised explosive device (IED) wounds—caused by an object from a IED or propelled by a IED driving into or through the body. There may be two wounds, one at the site of entry and one at the site of exit;

Mortar attack wounds—caused by an object from a mortar or propelled by a mortar driving into or through the body. There may be two wounds, one at the site of entry and one at the site of exit;

Missile attack wounds—caused by an object from a missile or propelled by a missile driving into or through the body. There may be two wounds, one at the site of entry and one at the site of exit;

Rocket propelled grenade (RPG) wounds—caused by an object from a RPG or propelled by a RPG driving into or through the body. There may be two wounds, one at the site of entry and one at the site of exit;

Grenade wounds—caused by an object from a grenade or propelled by a grenade driving into or through the body. There may be two wounds, one at the site of entry and one at the site of exit;

Bomb wounds—caused by an object from a bomb or propelled by a bomb driving into or through the body. There may be two wounds, one at the site of entry and one at the site of exit;

Land mine wounds—caused by an object from a land mine or propelled by a land mine driving into or through the body. There may be two wounds, one at the site of entry and one at the site of exit;

Any military or improvised ordinance wounds—caused by an object from any military or improvised ordinance or propelled by any military or improvised ordinance driving into or through the body. There may be two wounds, one at the site of entry and one at the site of exit.

Non-penetrating wounds can be classified into a number of different types. The types of non-penetrating wounds that can be treated with the present formulations can include, but are not limited to, First-degree abrasions involving only epidermal injury;

Second-degree abrasions involving the epidermis as well as the dermis;

Third-degree abrasions involving damage to the subcutaneous layer and the skin;

First-degree burns involving only epidermal injury

Second-degree burns involving the epidermis as well as the dermis;

Third-degree burns involving damage to all layers of the skin;

Fourth-degree burn involving damage to all layers of the skin and deeper tissues; and Skin grafts.

The burns can be classified into a number of different types, according to the object that caused the wound. For example, the burn can be a thermal burn, chemical burn, electrical burn, or radiation burn. In some embodiments, the composition including IL-10 may be a gel, lotion, cream or ointment that may be applied to a burn area. In some embodiments, the composition including IL-10 may be a gel, lotion, cream or ointment including a hydrogel that may be applied to the burn area.

In some embodiments, the prevention or reduction of scarring afforded by an extended release biocompatible composition encompasses any reduction in scarring as compared to the level of typically observed for a similar wound that is not treated with the extended release biocompatible composition. In some embodiments, the prevention or reduction of scarring afforded by an extended release biocompatible composition including IL-10 encompasses any reduction in scarring as compared to the level of typically observed for a similar wound that is treated with IL-10 without extended release properties.

In some embodiments, the extended release biocompatible composition may prevent or reduce scarring in the intraabdominal cavity, kidney, lung, or liver. In some embodiments, the extended release biocompatible composition may prevent or reduce scarring in the dermal layer or epidermis. In some embodiments, the extended release biocompatible composition may be used to accelerate healing and reduce scarring of the skin.

In considering the macroscopic appearance of a scar resulting from a treated wound, the extent of scarring, and hence the magnitude of any reduction in scarring achieved, may be assessed with reference to any of a number of parameters.

Suitable parameters for the macroscopic assessment of scars may include, but are not limited to, color of the scar; height of the scar; surface texture of the scar; and stiffness of the scar. Additional parameters for assessment of scars may include, but are not limited to, weave appearance of the collagen in the dermis, reconstitution of dermal appendages, number and appearance of sebaceous glands, and number and appearance of hair or hair follicles.

Some embodiments provide a composition and method for wound healing where the wound area has features of normal skin after treatment of a wound with the composition. In some embodiments, the features may be aesthetic appearance of the skin surface, barrier function, or tensile strength. In some embodiments, the features may be that all layers present in normal epidermis are present in the epidermis of the treated wound where in a scar not all layers of the epidermis are typically present.

In some embodiments, the features may be dermal appendages that are found in normal skin but are not typically found in a wound area that has not been treated. Typically dermal appendages are significantly reduced in a scar area. In some embodiments, the dermal appendages may be hair, hair follicles, arrector pilli, sebaceous glands or sweat glands. In some embodiments, the dermal appendages may be hair and hair follicles. In some embodiments, the dermal appendages may be sebaceous glands or sweat glands.

In some embodiments, the wound may be the result of a thermal burn, chemical burn, electrical burn, or radiation burn. In some embodiments, the composition may be a gel, lotion, cream or ointment that may be applied to a burn area.

In some embodiments, the composition includes IL-10. In some embodiments, the morphology of the epidermal surface of the wound area after treatment is similar to the morphology of the epidermal surface of normal skin. In some embodiments, the epidermal height of the wound area after treatment with the composition is similar to the epidermal height of normal skin. In some embodiments, the orientation of the nucleus of the basal keratinocytes of the wound area after treatment with the composition is similar to the orientation of the nucleus of the basal keratinocytes of normal skin.

In some embodiments, the composition may be an extended release biocompatible composition including a biodegradable support scaffold; and IL-10. In some embodiments, the amount of IL-10 in the composition is from about 0.2 µM to about 2.5 µM. In some embodiments, the composition is administered in a single dosage and provides features of normal skin after treatment of a wound in a wound area after a period of time. In some embodiments, the features in the wound area are evaluated using an Assessment Scale value to obtain an Assessment Scale score. In some embodiments, the biodegradable support scaffold comprises hyaluronan or a hyaluronan moiety. In some embodiments, the hyaluronan is hyaluronic acid. In some embodiments, the biodegradable support scaffold comprises a heparin or heparan sulfate. In some embodiments, the biodegradable support scaffold comprises collagen. In some embodiments, the collagen is human collagen. In some embodiments, the collagen is Type-I collagen. In some embodiments, the collagen is Type-III collagen. In some embodiments, the collagen is Type-I collagen, Type-II collagen or Type-III collagen, or any combination thereof. In some embodiments, the biodegradable support scaffold comprises PEG or a PEG moiety. In some embodiments, the extended release biocompatible composition including a biodegradable support scaffold; and IL-10 and method for wound healing provides features of normal skin after treatment of a wound that is improved compared to a composition that includes biodegradable support scaffold without IL-10. In some embodiments, the extended release biocompatible composition including a biodegradable support scaffold and IL-10, and the method for wound healing using such composition, restores dermal appendages at a level greater than the dermal appendages restored in scar formation without treatment or in wound treatment with a composition that does not include IL-10. In some embodiments, a wound will heal to have dermal appendages to the level of generally observed for normal skin. In some embodiments, a wound will heal to restore at least two dermal appendages to a level of 50% or greater than generally observed for normal skin as assessed with reference to at least two of the parameters set out herein or otherwise known in the art.

In some embodiments, the biodegradable support scaffold provides beneficial effects without IL-10 and the IL-10 provides beneficial effects without the biodegradable support scaffold and a composition including both a biodegradable support scaffold and IL-10 has a greater beneficial effect than would be achieved by separate treatment of the wound with biodegradable support scaffold and IL-10. In some embodiments, the biodegradable support scaffold provides beneficial effects without IL-10 and the IL-10 provides beneficial effects without the biodegradable support scaffold and a composition including both a biodegradable support scaffold and IL-10 has a greater beneficial effect than would be achieved by separate treatment of the wound with biodegradable support scaffold and IL-10 using a mouse model to evaluate the beneficial effect. In some embodiments, the beneficial effect of the composition including both a biodegradable support scaffold and IL-10 is 10% or greater, 20% or greater, 30% or greater, 40% or greater, 50% or greater, 60% or greater, 70% or greater or 80% or greater than would be achieved by separate treatment of the wound with biodegradable support scaffold and IL-10. In some embodiments, the beneficial effect of the composition including both a biodegradable support scaffold and IL-10 is 10% or greater, 20% or greater, 30% or greater, 40% or greater, 50% or greater, 60% or greater, 70% or greater or 80% or greater than would be achieved by separate treatment of the wound with biodegradable support scaffold and IL-10 using a mouse model to evaluate the beneficial effect. In some embodiments, the beneficial effect of the composition including both a biodegradable support scaffold and IL-10 is 10% or greater, 20% or greater, 30% or greater, 40% or greater, 50% or greater, 60% or greater, 70% or greater or 80% or greater than would be achieved by treatment of the wound with biodegradable support scaffold and no IL-10. In some embodiments, the beneficial effect of the composition including both a biodegradable support scaffold and IL-10 is 10% or greater, 20% or greater, 30% or greater, 40% or greater, 50% or greater, 60% or greater, 70% or greater or 80% or greater than would be achieved by treatment of the wound with biodegradable support scaffold and no IL-10 using a mouse model to evaluate the beneficial effect. In some embodiments, the beneficial effect of the composition including both a biodegradable support scaffold and IL-10 is 10% or greater, 20% or greater, 30% or greater, 40% or greater, 50% or greater, 60% or greater, 70% or greater or 80% or greater than would be achieved by treatment of the wound with IL-10 and no biodegradable support scaffold. In some embodiments, the beneficial effect of the composition including both a biodegradable support scaffold and IL-10 is 10% or greater, 20% or greater, 30% or greater, 40% or greater, 50% or greater, 60% or greater, 70% or greater or 80% or greater than would be achieved by treatment of the wound with IL-10 and no biodegradable support scaffold using a mouse model to evaluate the beneficial effect. In some embodiments, the beneficial effect of the composition including both a biodegradable support scaffold and IL-10 is 10% or greater, 20% or greater, 30% or greater, 40% or greater, 50% or greater, 60% or greater, 70% or greater or 80% or greater than would be achieved by separate treatment of the wound with biodegradable support scaffold and IL-10. In some embodiments, the beneficial effect may be aesthetic appearance of the skin surface, barrier function, tensile strength, or a combination thereof. In some embodiments, the beneficial effect may be that all layers present in a normal epidermis are present in the treated epidermis where in a scar not all layers present in a normal epidermis are typically present. In some embodiments, the beneficial effect may be the treated wound area having dermal appendages at a level closer to normal skin than the dermal appendages present in a wound area that has not been treated or that has not been treated with the compositions and methods provided herein. In some embodiments, the beneficial effect may be hair, hair follicles, arrector pilli, sebaceous glands or sweat glands in the wound area that are found in normal skin but are not typically found, or are found in reduced levels compared to a wound area that has not been treated or that has not been treated with the compositions and methods provided herein. In some embodiments, the dermal appendages may be hair and hair follicles. In some embodiments, the dermal appendages may be sebaceous glands or sweat glands.

In some embodiments, the parameters can be evaluated using an Assessment Scale where an Assessment Scale value (INDEX) is obtained. In some embodiments, the Assessment Scale value (INDEX) for each parameter may be used to obtain an Assessment Scale Score where the Assessment Scale Score=("Σ INDEX/n)×100 where n is the number of parameters being evaluated and a score of 100 would be a scar that is indistinguishable from normal skin (or un-injured skin). In some embodiments, n may be 2, 3 4, 5 or 6. In some embodiments, a score of greater than 50 shows an improvement over normal scarring. In some embodiments, at least one epidermal and at least one dermal parameter may be evaluated. In some embodiments, the scar is evaluated in a mouse model. In some embodiments, the mice used in the mouse model are C57Bl/6J mice. In some embodiments, the scar is evaluated on day 28 after wounding. In some embodiments, the wounds are harvested at 30 and 90 days and assessed.

In some embodiments, the wound treatment result provides an Assessment Scale score of 50 to 80. In some embodiments, the Assessment Scale score may be 50 to 70. In some embodiments, the Assessment Scale score may be 50 to 60. In some embodiments, the Assessment Scale score may be about 50. In some embodiments, the Assessment Scale score may be 80 to 130. In some embodiments, the Assessment Scale score may be 90 to 120. In some embodiments, the Assessment Scale score may be 100 to 110. In some embodiments, the Assessment Scale score may be up to 200

In some embodiments, a wound will heal to have less scarring compared to the level of generally observed for a similar wound that is not treated with the extended release biocompatible composition and will demonstrate a reduction in scarring as assessed with reference to at least one of the parameters for macroscopic assessment set out herein or otherwise known in the art. In some embodiments, a wound will heal to have less scarring compared to the level of generally observed for a similar wound that is not treated with the extended release biocompatible composition and will demonstrate a reduction in scarring as assessed with reference to at least two of the parameters for macroscopic assessment set out herein or otherwise known in the art. In some embodiments, a wound will heal to have less scarring compared to the level of generally observed for a similar wound that is not treated with the extended release biocompatible composition and will demonstrate a reduction in scarring as assessed with reference to at least three of the parameters for macroscopic assessment set out herein or otherwise known in the art. In some embodiments, a wound will heal to have less scarring compared to the level of generally observed for a similar wound that is not treated with the extended release biocompatible composition and will demonstrate a reduction in scarring as assessed with reference to all of the parameters for macroscopic assessment set out herein or otherwise known in the art.

Suitable parameters for the microscopic assessment of scars may include, but are not limited to, thickness of extracellular matrix fibers; orientation of extracellular matrix fibers; extracellular matrix fibers composition of the scar; and cellularity of the scar.

In some embodiments, a wound will heal to have less scarring compared to the level of generally observed for a similar wound that is not treated with the extended release biocompatible composition and will demonstrate a reduction in scarring as assessed with reference to at least one of the parameters for microscopic assessment set out herein or otherwise known in the art. In some embodiments, a wound will heal to have less scarring compared to the level of generally observed for a similar wound that is not treated with the extended release biocompatible composition and will demonstrate a reduction in scarring as assessed with reference to at least two of the parameters for microscopic assessment set out herein or otherwise known in the art. In some embodiments, a wound will heal to have less scarring compared to the level of generally observed for a similar wound that is not treated with the extended release biocompatible composition and will demonstrate a reduction in scarring as assessed with reference to at least three of the parameters for microscopic assessment set out herein or otherwise known in the art. In some embodiments, a wound will heal to have less scarring compared to the level of generally observed for a similar wound that is not treated with the extended release biocompatible composition and will demonstrate a reduction in scarring as assessed with reference to all of the parameters for microscopic assessment set out herein or otherwise known in the art.

While not wishing to be bound by the following, it is believed that the extended release biocompatible compositions as disclosed and described herein provide wound healing properties beyond those of any heretofore used formulations by virtue of the sustained release of IL-10 in the present compositions. Single injection of an extended release biocompatible composition including IL-10 provides superior wound healing properties in comparison to single injection of IL-10 not included in an extended release formulation. In addition, it is believed that, by providing both the ability to initiate the wound healing response and to sustain the wound healing response, the compositions and methods provided herein provide particular advantages over present compositions. Further, it is believed that the hyaluronan-containing biocompatible compositions as disclosed and described herein provide wound healing properties beyond those of any heretofore used formulations by virtue of the synergistic effect provided by the combination of hyaluronan IL-10. Single injection of extended release biocompatible composition including IL-10 and hyaluronan provides superior wound healing properties in comparison to single injection of IL-10 without hyaluronan.

Suitable parameters for the clinical measurement and assessment of scars may be selected based upon a variety of measures or assessments including those described by Beausang et al. (A new quantitative scale for clinical scar assessment. Plast Reconstr Surg., 1998, 102: 1954-1961) and van Zuijlen et al. (Scar assessment tools: implications for current research. Plast Reconstr Surg., 2002, 109(3): 1108-1122). For example, suitable parameters include, but are not limited to, assessment with regard to Visual Analogue Scale (Vas) Scar Score; scar height, scar width, scar perimeter, scar area or scar volume; appearance and/or color of scar compared to surrounding unscarred skin; scar distortion and mechanical performance; and scar contour and scar texture.

In some embodiments, the extended release biocompatible composition may be administered to a wound site that provides a first amount of IL-10 at the wound site during a first time period and provides a second amount of IL-10 at the wound site during a second time period.

Some embodiments relate to an extended release biocompatible composition that upon administration can result in a maximum concentration (Tmax) at the wound site during a bolus time period measured from initial administration of composition. In some embodiments, the extended release biocompatible composition upon administration can result in a Tmax of IL-10 from about 0.05 ng/mL to about 10000 ng/mL to the tissue at the wound site during the bolus time period measured from initial administration of composition.

It is understood that during the administration period the wound may heal and no longer actually be considered to be a wound.

In any of the embodiments disclosed and described herein, IL-10 related peptides disclosed in US. Publication No. 2008/0139478 may be included in the compositions and methods in place of IL-10. For example, SEQ. ID 1 or SEQ. ID 2 disclosed in US. Publication No. 2008/0139478 may be included in the compositions and methods in place of IL-10.

In any of the embodiments disclosed and described herein, a fragment or partially modified form of IL-10 disclosed in U.S. Pat. No. 7,052,684 may be included in the compositions and methods in place of IL-10. For example, a fragment or partially modified form of IL-10 may have at least 40% homology with IL-10. In some embodiments, the fragment or partially modified form of IL-10 may have at least 50, 60, 70, 80, 90 or 95% homology with IL-10.

EXAMPLES

Example 1: Preparation of Extended Release Biocompatible Composition

Composition 1 is prepared by mixing high molecular weight hyaluronan (HA), heparin sulfate and rIL-10 to prepare a mixture. The mixture is combined with PEG diacrylate and Type I collagen. Subsequently, the HA is chemically cross-linked with PEG diacrylate forming a stable matrix. Type I collagen may improve the gel quality for in vitro experiments.

Figure 1B:
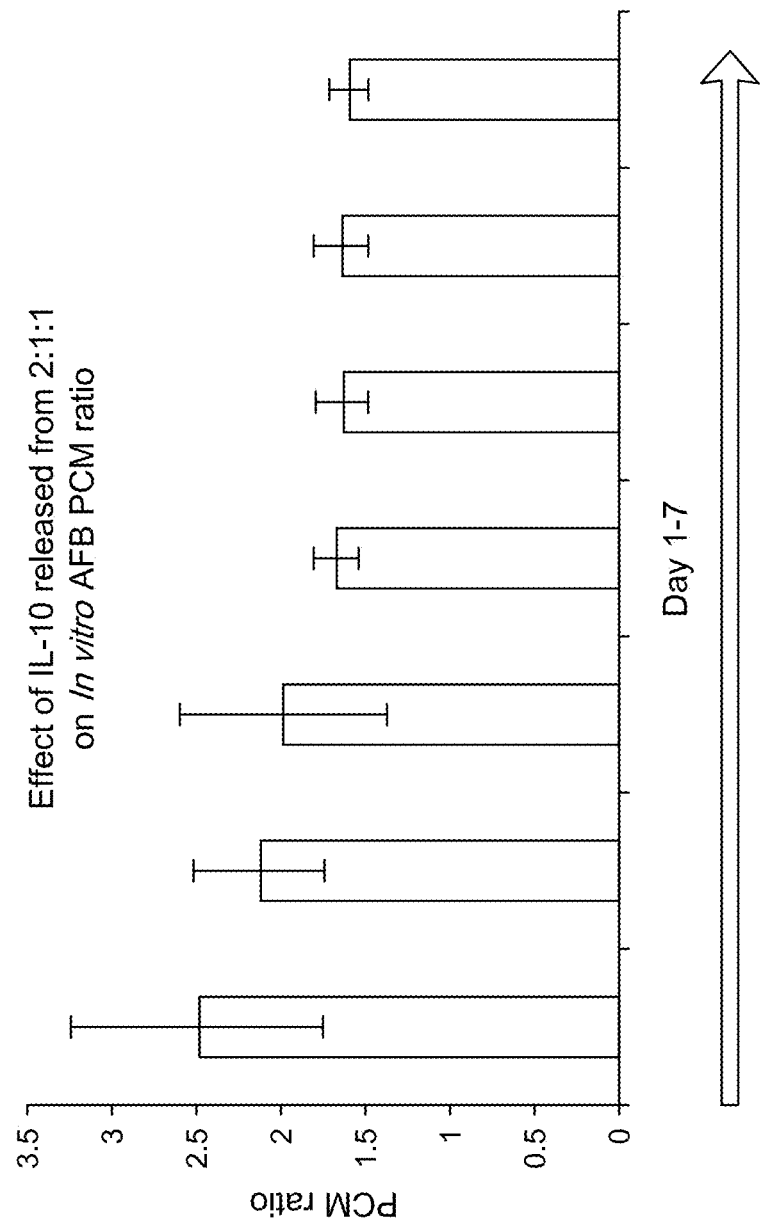

It was determined that a ratio of 2:1:1 (HA:Collagen:cross-linker) results in sustained release of rIL-10 in vitro for seven days. FIG. 1A shows HH10 (purple line) in vitro can result to sustained delivery of IL-10 for 7 days. To evaluate the biologic activity of the released rIL-10 from the composition, its ability to induce HA rich pericellular matrix (PCM) formation by postnatal dermal fibroblasts was assessed. To test the biologic activity of the rIL10 released by composition 1, gels (25 µL loaded with 800 ng of rIL-10) were placed in cell culture wells in media (250 µL, Dulbecco's Modified Eagle Medium, Life Technologies Corporation, Carlsbad, Calif.), which was changed daily. The conditioned media from each daily change was then added to postnatal dermal fibroblasts in cell culture which resulted in the formation of large HA rich pericellular matrices formed by the dermal fibroblasts for up to seven days demonstrating the intact biologic activity of the rIL-10 released by HH10. FIG. 1B shows IL-10 released from HH10 induces large HA rich PCM by adult fibroblasts for up to 7 days.

Example 2: Evaluation of Composition 1

Figure 2A:
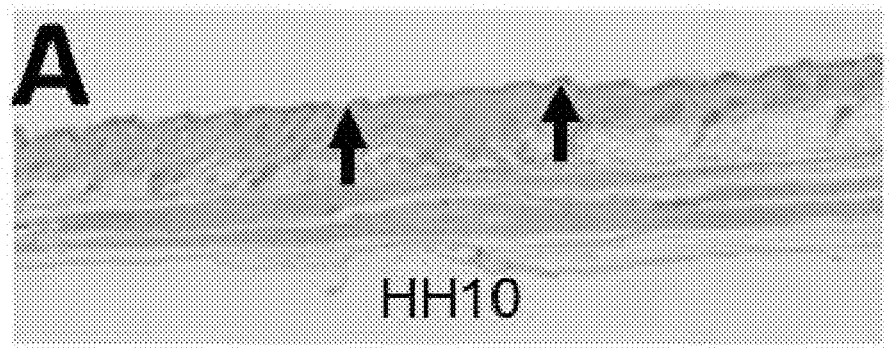
FIG. 2(A)-(F) depict scar suppression and wound healing by sustained release of IL-10.
Figure 2B:
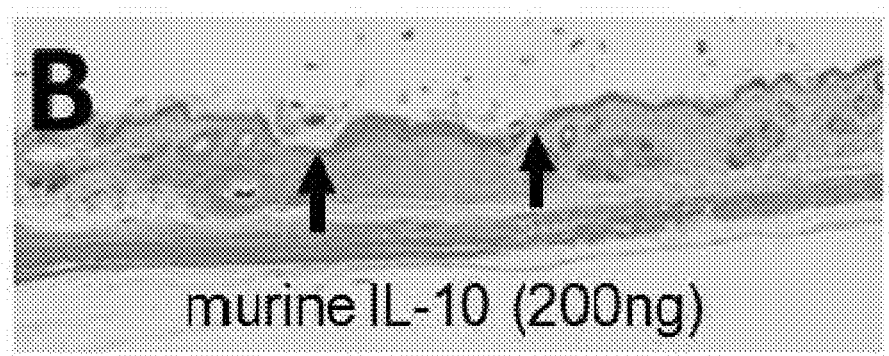
Figure 2C:
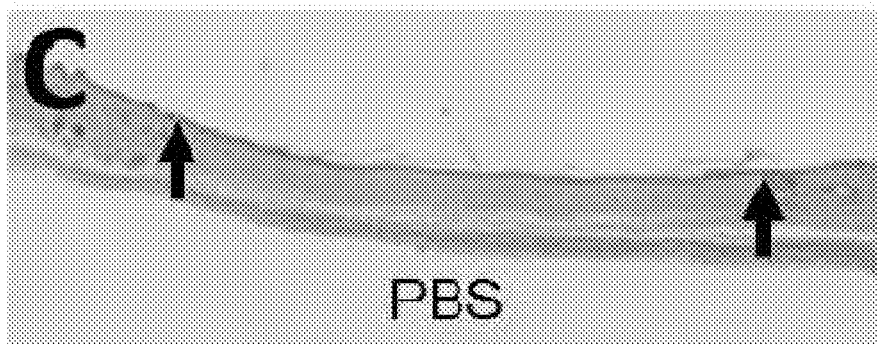
Figure 2D:
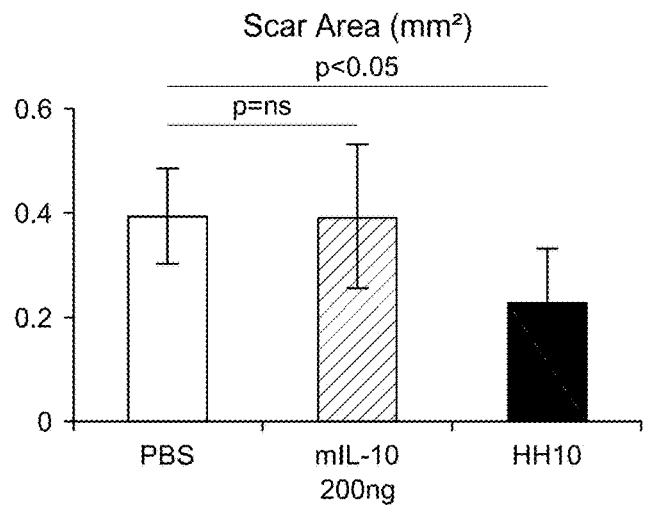
Figure 2E:
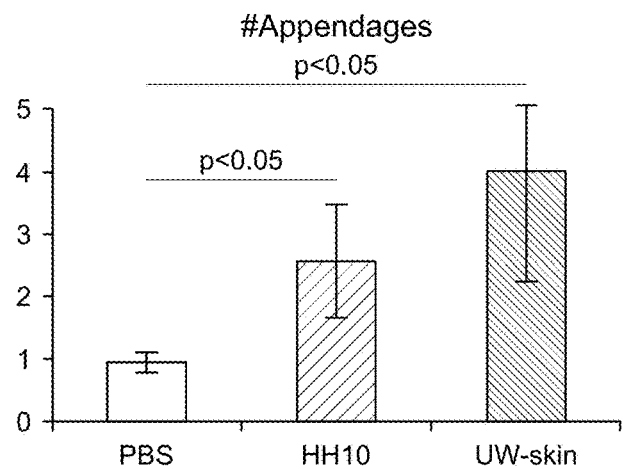
Figure 2F:
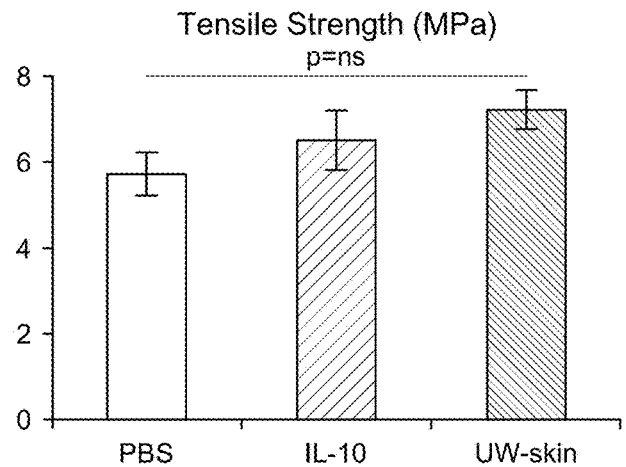

Composition 1 induces skin regeneration and prevents wound scaring in mice. FIG. 2A shows HH10 results in wound healing that is indistinguishable from the surrounding skin. FIG. 2B shows rIL-10 also attenuates scar formation to a much lesser degree; both compared to PBS treated wounds (FIG. 2C). The black arrows mark the area of the residual wound HH10 reduces scar area (FIG. 2D) and increases the number of dermal appendages (FIG. 2E) at 30 days compared to both rIL-10 or PBS control with skin integrity, (tensile strength) that is statistically no different than unwounded skin (FIG. 2F). For example, administration of a single dose of Composition 1 (loaded with 800 ng/mL of IL-10) results in a regenerative wound repair at 30 (FIG. 2A) and 90 days compared to both PBS (FIG. 2B) control treated wounds and wounds treated with a single dose of recombinant IL-10 (200 ng) (FIG. 2C) in C57Bl/6J mice. Wound treated with Composition 1 (FIG. 2A) have similar basket weave appearance of the collagen in the dermis, reconstitution of dermal appendages and a normal appearing epidermis to uninjured skin. Treatment with Composition 1 results in a significant reduction of scar area at 30 days compared to controls and significant increase in dermal appendages (hair follicles) to levels not significantly different to unwounded skin (FIG. 2D-E). Similarly, IL-10 results in wound healing with similar biomechanical properties compared to unwounded skin, including tensile strength (FIG. 2F), stiffness and modulus.

Example 3: Murine Excisional Wound Healing Model I

A murine excisional wound healing model is used to evaluate Composition 1 C57BL/6j mice are shaved and prepared; two 4 mm full thickness wounds are created using a dermal punch biopsy on the flanks. These wounds are labeled with India ink and a sterile transparent dressing are placed over the wound. Twenty-five microliters of Composition 1 or control treatments are injected into the wound well. In a separate group of animals, a silicone stent of 6-mm inner diameter is secured around the wounds using instant Krazy glue and interrupted 6-O nylon sutures to control for contracture in loose skinned murine wounds. Animals are housed individually.

Forty mice having bilateral wounds created with and without the silicone stents to control for contracture are evaluated. Wounds are harvested at 30 and 90 days and assessed for regenerative healing.

Tissue Handling/Processing:

At 30 and 90 days post wounding, mice are shaved and the wound site is identified by the India ink staining. Wound is harvested and then bisected in a vertical axis to maintain consistent wound orientation for scar analysis. Wounds are fixed overnight in 10% neutral buffered formalin, processed and paraffin embedded. 5 μm sections are collected and stained with H&E and Masson's trichrome to analyze wound repair outcomes.

Regenerative Wound Healing Analysis:

To assess regenerative wound healing, both H&E and trichrome sections are analyzed by the following parameters: 1) scar width, height and area as calculated with computer assisted morphometry, 2) evaluation of the epidermis by epidermal height and epidermal flatness, and 3) quantification of dermal appendages. Each of these wound repair parameters are given a numeric score. These scores are fitted using the Minitab software, and the data is extrapolated to predict the optimal formulation of Composition 1 that will yield maximal wound healing efficacy.

Biomechanical Testing:

To assess wound/skin integrity, tensile testing is performed. 35 mm×6 mm-templated rectangular skin samples with wounds in the middle in between intact skin segments are harvested after 30 and 90 days. The edges are placed in custom grips attached to an electromechanical testing system with a 10 Newton (N) load cell. Apparent wound stiffness is determined as the slope (in N/m) of the load-elongation curve in the linear region, and the maximum tensile force before wound failure is recorded (FIG. 2B).

Example 4: Murine Excisional Wound Healing Model II

A murine excisional wound healing model is used to evaluate toxicology of Composition 1. Two 4 mm full thickness wounds are prepared using a dermal punch biopsy on the flanks into 30 C57bl/6j mice. Mice (10/group) are treated without Composition 1 (control) or Composition 1 at a selected dosage administered once on day 0, or daily to the same wound for 10 straight days. Five animals per group are sacrificed on day 10 and on day 17, allowing for a 7-day recovery phase for each group.

Gross Observations.

Gross observations as a measurement of drug safety are conducted daily throughout the study and include the following: respiration, posture, activity, pallor, and weight.

Hematology.

Hematology is performed on serum samples collected at 0, 48 hr, day 7 and day 14. Hematology readouts include: leukocyte count, erythrocyte count, hemoglobin, hematocrit, MCH, MCV, MCHC, platelet count, differential count, cellular morphology, and reticulocyte count.

Biochemistry.

Clinical chemistry readouts include: alkaline phosphatase, ALT, AST, CK, albumin, total protein, globulin, total bilirubin, direct bilirubin, indirect bilirubin, BUN, creatinine, cholesterol, glucose, calcium, phosphorus, $TCO_2$, chloride, potassium, sodium, NA/K ratio, A/G ratio and B/C ratio.

Histopathology.

Histopathological examination is performed on the following selected tissues at the end of in-life of the study: skin, liver, kidney, lung, heart, spleen, and pancreas. Tissues are fixed in 10% neutral buffered formalin, embedded in paraffin and stained with hematoxylin and eosin stains. Samples are evaluated by light microscopy and scored by a Study Pathologist using standard methods.

A total of 30 C57bl/6j wild-type mice are used to complete the study taking up to 3 months for completion.

Example 5: rhIL-10 Binding/Release Kinetics Assay

Composition 1 is solidified with between 1.0 to 40 ug/ml of rhIL-10 in 48-well plates for 1 hour at room temperature. Composition 1 is washed one time with 250 μL of PBS-BSA to remove any unbound rhIL-10. The total amount of unbound rhIL-10 collected in the PBS-BSA wash for each well is determined using ELISA. After the PBS-BSA wash, each well receives 250 uL of fresh PBS-BSA. The plates are incubated at 37° F. degrees for 14 days. Starting on day 0, and every 2 days up to 14 days, 100 μL of supernatant is removed from a new set of triplicate wells, and analyzed for the amount of free rhIL-10. The level of free rhIL-10 in the PBS-BSA at day 0 acts as the baseline control. In addition, negative control wells consisting of the same hydrogel formulation included in Composition 1, but without rhIL-10, will act as the daily controls.

Example 6: rhIL-10 Potency Assay

Composition 1 is cultured in 48-well tissue culture plates at 37° F. for 14 days. Supernatants (100 μL) from the Composition 1 culture wells are harvested on days 0, 7 and 14. The concentration of rhIL-10 in the supernatants will be determined using ELISA. The biological activity of the rhIL-10 release from Composition 1 is determined by measuring the proliferative response of MC/9 cells (ATCC #CRL-8306). MC/9 cells are a mouse mast cell line that proliferates in response to rhIL-10 in the presence of IL-4. This cell line is commonly used to quantify rhIL-10 potency. A typical $EC_{50}$ of fully active hIL-10 is expected to be in the range of 0.1 to 1 ng/mL. The assay provides biological activity of rhIL-10 released from Composition 1 may be equal to the biological activity of rhIL-10 prior to inclusion in Composition 1. MC/9 proliferation is measured using a colorimetric dye reduction assay (MTT, Sigma) in a 96 well format.

Example 7: Extended Release Biocompatible Composition 2

Composition 2 is prepared in a similar manner to that described in Example 1 where the amount of IL-10 in the composition is from about 0.2 µM to about 2.5 µM.

Example 8: Evaluation of Composition 2

The effect of Composition 2 (which includes IL-10) on wound healing has been compared to the extended release biocompatible composition without IL-10. Several dermal and epidermal parameters have been studied to identify the effect of scaffold only (gel control) vs. extended release biocompatible composition (Composition 2) on cutaneous wound repair. The parameters include the quantification of epidermal height and the nuclear orientation of the basal keratinocytes in the epidermis; and the quantification of the scar area, dermal appendages and vessel density in the dermis of the wounds. The data is compared to unwounded skin, characteristic scar and regenerative wound healing observed in wounds treated with lentiviral overexpression of IL-10 at the wound site.

The differences between murine uninjured skin and a scar are histologically very distinct. Murine skin has 2 major layers, the epidermis and the dermis. Several quantifiable parameters were identified in the epidermis as well as in the dermis that can be used to evaluate the differences in the extent of scarring in murine cutaneous wounds. The parameters include i) the quantification of topography, ii) epidermal height, and iii) the nuclear orientation of the basal keratinocytes in the epidermis; and iv) the quantification of the scar area, v) dermal appendages, and vi) vascularity (vessel density) in the dermis of the scars. Each of these parameters is measured in the central ½ portion of the scar being evaluated.

The wound samples are harvested with the wound in the middle surrounded by intact uninjured skin. The entire wound/scar is divided into 4 quarters and the central 2 portion of the scar is evaluated for the different dermal and epidermal parameters.

Epidermal Parameters
Topographical Score:

This is based on the morphology or the undulation pattern of the epidermal surface. Histologically the surface of the uninjured skin has more undulations as compared to the scar which gives the scar its characteristic flat appearance. The epidermal length is measured per 200 µm of grid length (measured in 3-6 200 µm fields per sample).

Epidermal Height:

The epidermal height is measured as the height from epidermal-dermal junction to top of the epidermis. Epidermal height is usually more in the area of the scars as compared to the skin, and it is measured in µm (3 measurements per 200 µm grid).

Orientation of the Nucleus of the Basal Keratinocytes:

The polarity of the epidermal cell, is measured in terms of Sin θ, where θ is the angle between the line through the long axis of the nucleus of the basal cell and the epidermal-dermal junction. The maximum value is one. In case of skin, the cells being more columnar in shape and oriented perpendicular to the epidermal-dermal junction, Sin θ is closer to one, and in scars, the cells being more flattened and parallel to the epidermal-dermal junction, have a value less than one.

Dermal Parameters
Scar Area:

Histologic wound sections are scanned from edge to edge. Computer assisted morphometric image analysis is used to measure the total scar area (measured in square micrometers) per each wound section.

Dermal Appendages:

Adnexal structures including hair follicles, sabaceous (oil) glands and sweat glands are observed in uninjured skin. Dermal appendages are significantly reduced in scars as compared to uninjured skin. The number of dermal appendages per 200 µm grid (measured in 3-6 200 µm fields per sample) is measured and compared to uninjured skin.

Vascular Density:

Vascularity is less in the scar compared to the normal uninjured skin. The number of CD31-positive lumens per 200 µm grid (measured in 3-6 200 µm fields per section) is measured.

The parameters can be evaluated using an Assessment Scale where the parameters in the treated area may be compared to parameters in a normal skin area and/or parameters in an untreated scar area after a period of time. For each parameter an Assessment Scale value (INDEX) may be obtained. In some embodiments, INDEX=[(treated wound area parameter-untreated wound area parameter)/(non-wounded area parameter-untreated wound area parameter)] or mathematical equivalent thereof. In some embodiments, the treated area may be histologically closer in at least two parameters to normal skin than it is to untreated scar area. In some embodiments, the Assessment Scale value of two or more parameters may be used to calculate an Assessment Scale score. In some embodiments, the Assessment Scale Score=("Σ INDEX/n)×100 where n is the number of parameters being evaluated and a score of 100 would be a treatment result that provides a "scar" that is indistinguishable from normal skin (or un-injured skin). In some embodiments, n may be 2, 3 4, 5 or 6. In some embodiments, a score of greater than 50 shows an improvement over normal scarring. In some embodiments, the wound treatment result provides a score of greater than 60. In some embodiments, the wound treatment result provides a score of greater than 70. In some embodiments, the wound treatment result provides a score of greater than 80. In some embodiments, the wound treatment result provides a score of greater than 90. In some embodiments, the score is about 50, 60, 70, 80, 90, 100, 110, 120, 130 or 200, or within a range defined by any two of the preceding values. In some embodiments, at least one epidermal and at least one dermal parameter may be evaluated. In some embodiments, the scar is evaluated in a mouse model. In some embodiments, the mice used in the mouse model are C57Bl/6J mice. In some embodiments, the scar is evaluated on day 28 after wounding. In some embodiments, the wounds are harvested at 30 and 90 days and assessed.

In some embodiments, the non-wounded area parameter is a standard parameter value for age of patient. In some embodiments, the age of the patient may be from about 1 day old to about 10 days old. In some embodiments, the age of the patient may be from about 10 days old to about 1 month old. In some embodiments, the age of the patient may be from about 1 month old to about six months old. In some embodiments, the age of the patient may be from about six months old to about 1 year old. In some embodiments, the age of the patient may be from about 1 year old to about 2 years old. In some embodiments, the age of the patient may be from about 2 years old to about 6 years old. In some embodiments, the age of the patient may be from about 6 years old to about 16 years old. In some embodiments, the age of the patient may be from about 16 years old to about 26 years old. In some embodiments, the age of the patient may be from about 26 years old to about 36 years old. In some embodiments, the age of the patient may be from about 36 years old to about 56 years old. In some embodiments, the age of the patient may be from about 56 years old to about 76 years old. In some embodiments, the age of the patient may be from about 76 years old to about 96 years old or greater. In some embodiments, the treatment result provides a score of greater than 60. In some embodiments, a score of greater than 70. In some embodiments, a score of greater than 80. In some embodiments, a score of greater than 90. In some embodiments, the score is about 50, 60, 70, 80, 90, 100, 110, 120, 130 or 200, or within a range defined by any two of the preceding values.

Evaluation of Wounded Skin

Figure 3A:
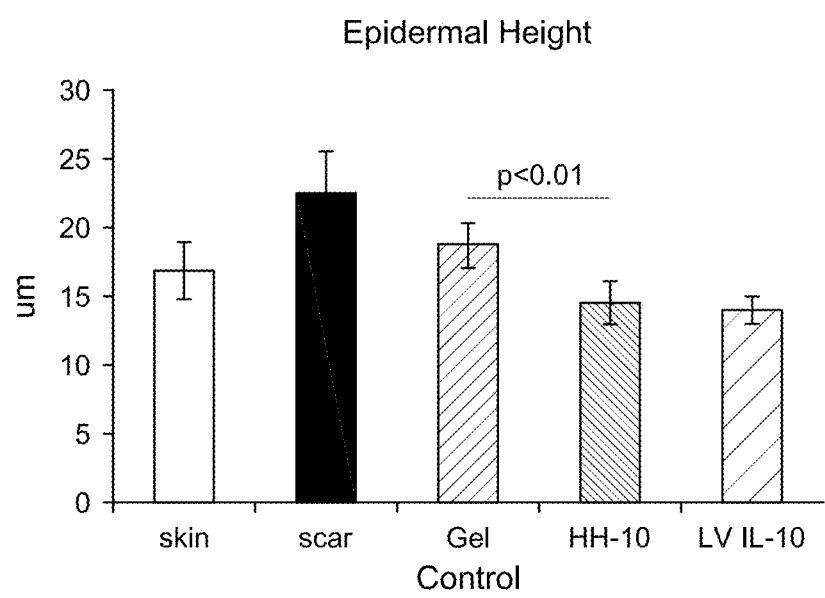
FIG. 3(A)-(E) compares epidermal and dermal parameters for treating wounds with gel only (control), Composition 2 (HH-10) and lentiviral over expression of IL-10 (LV IL-10).
Figure 3B:
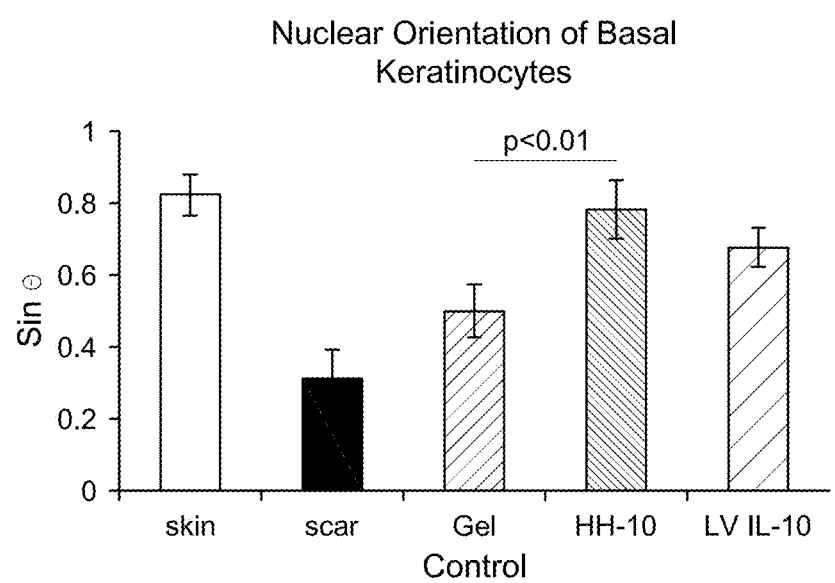
Figure 3C:
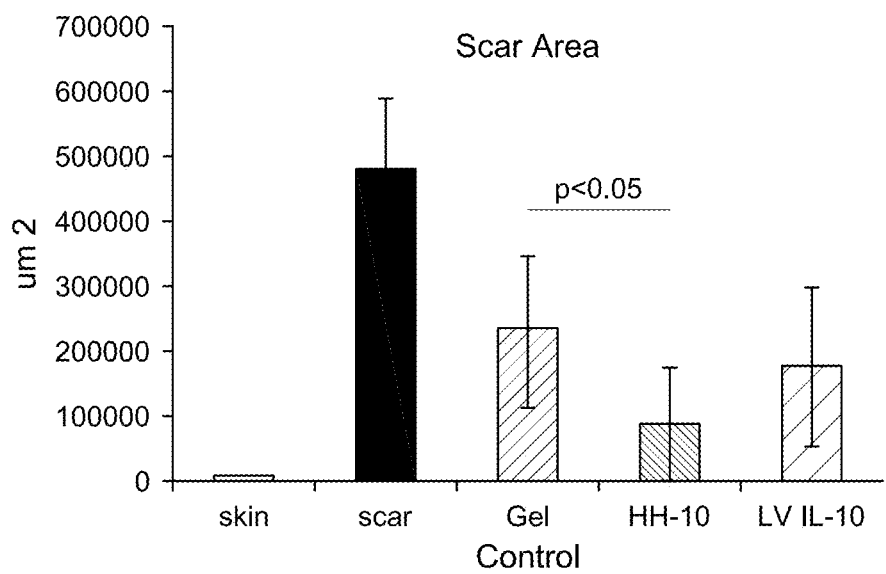
Figure 3D:
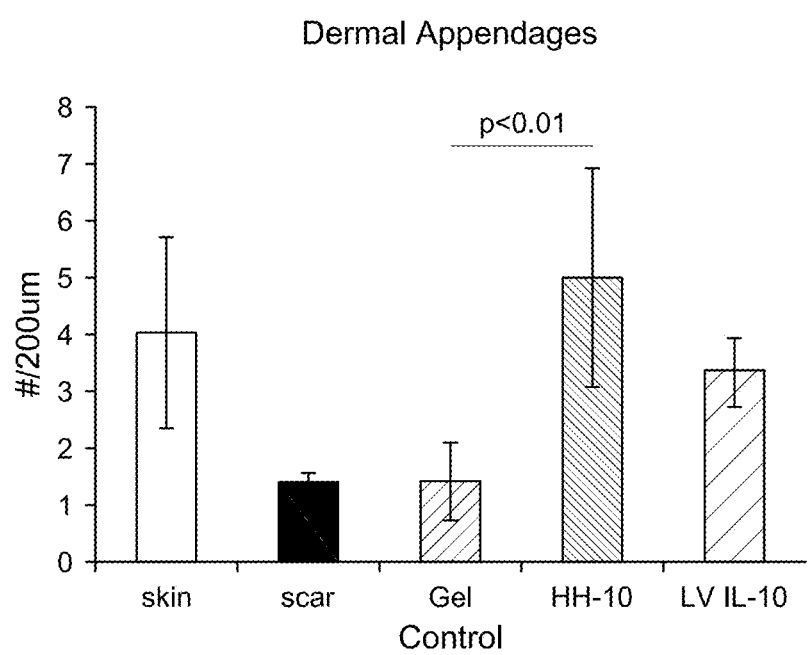
Figure 3E:
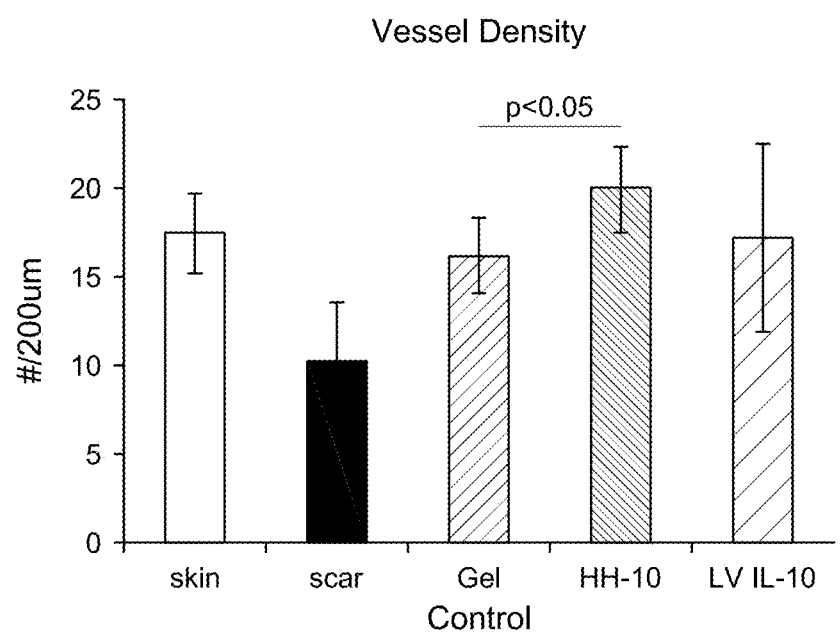

The treatment of wounds using gel only (control), HH-10 (Composition 2) and wounds treated with lentiviral over expression of IL-10 (LV IL-10) were compared to each other and unwounded skin and wounded skin that was untreated (scar) at day 28 post wounding. Several epidermal parameters and dermal parameters were evaluated. FIGS. 3A-B show quantification of epidermal height and the nuclear orientation of the basal keratinocytes in the epidermis of the wounds, and FIGS. 3C-E show quantification of scar area, dermal appendages and vessel density in the dermis of the wounds where the different treatments and controls are listed along the X-axis. Treatment with Composition 2 (HH10) results in significantly improved wound healing based on the observed parameters compared to gel only (control). Composition 2 (HH10) treated wound at day 28 post wounding, and gel control treated wound at day 28 post wounding were visually compared and Composition 2 (HH10) treated wounds are starting to appear similar to uninjured skin in terms of collagen arrangement, restoration of dermal appendages and epidermal structure at day 28. This may have implications for conditions where hair restoration would be advantageous.

Although the foregoing discussion touches on many particular aspects and features of the disclosure, the scope of the exclusive rights should not be limited to particular embodiments disclosed herein, but instead should be measured by the full, lawful, valid scope of the claims that follow.

What is claimed is:

1. An extended release biocompatible composition, comprising:
   a biodegradable support scaffold;
   and IL-10,
   wherein the biodegradable support scaffold comprises from 10% to 90% heparin or heparan sulfate, wherein the amount of IL-10 in the composition is from 0.2 µM to 2.5 µM.

2. The composition of claim 1, wherein the biodegradable support scaffold further comprises hyaluronan or a hyaluronan moiety.

3. The composition of claim 2, wherein the hyaluronan is hyaluronic acid.

4. The composition of claim 1, wherein the biodegradable support scaffold comprises heparan sulfate.

5. The composition of claim 1, wherein the biodegradable support scaffold further comprises collagen.

6. The composition of claim 5, wherein the collagen is human collagen.

7. The composition of claim 6, wherein the collagen is Type-I collagen.

8. The composition of claim 6, wherein the collagen is Type-III collagen.

9. The composition of claim 6, wherein the collagen is Type-I collagen, Type-II collagen or Type-III collagen, or any combination thereof.

10. The composition of claim 1, wherein the biodegradable support scaffold further comprises PEG or a PEG moiety.

11. The composition of claim 1, wherein the biodegradable support scaffold comprises disulfide linkages.

12. The composition of claim 1, wherein the biodegradable support scaffold comprises a cross-linker.

13. The composition of claim 12, wherein the cross-linker comprises a PEG moiety.

14. The composition of claim 1, wherein the amount of IL-10 in the composition is from 0.017 µM to 0.035 µM.

15. The composition of claim 1, wherein the biodegradable support scaffold comprises from 30% to 70% heparin or heparan sulfate.

16. The composition of claim 12, wherein the biodegradable support scaffold comprises from 15% to 40% cross-linker.

17. The composition of claim 1, wherein the extended release biocompatible composition comprises from 10% to 59% biodegradable support scaffold.

18. The composition of claim 1, wherein the amount of IL-10 in the composition is from 1 µM to 2.5 µM.

* * * * *